US008409853B2

(12) United States Patent
Dayton et al.

(10) Patent No.: US 8,409,853 B2
(45) Date of Patent: Apr. 2, 2013

(54) CONTINUOUS PROCESS AND APPARATUS FOR ENZYMATIC TREATMENT OF LIPIDS

(75) Inventors: Christopher L. G. Dayton, Bourbonnais, IL (US); Marcelo Augusto dos Santos, Gaspar (BR)

(73) Assignee: Bunge Oils, Inc., St. Louis, MO (US)

(*) Notice: Subject to any disclaimer, the term of this patent is extended or adjusted under 35 U.S.C. 154(b) by 852 days.

(21) Appl. No.: 12/499,052

(22) Filed: Jul. 7, 2009

(65) Prior Publication Data
US 2009/0317902 A1 Dec. 24, 2009

Related U.S. Application Data

(62) Division of application No. 11/567,318, filed on Dec. 6, 2006.

(51) Int. Cl.
C12M 1/00 (2006.01)

(52) U.S. Cl. .......... 435/294.1; 435/135; 435/134; 435/136; 435/196; 435/197; 435/198

(58) Field of Classification Search .......... 435/294.1, 435/135, 136, 196, 197, 198
See application file for complete search history.

(56) References Cited

U.S. PATENT DOCUMENTS

| | | | |
|---|---|---|---|
| 2,206,168 A | 7/1940 | Edeler et al. |
| 2,265,837 A | 12/1941 | Harding |
| 2,626,952 A | 1/1953 | Lange et al. |
| 3,142,545 A | 7/1964 | Raarup et al. |
| 3,154,481 A | 10/1964 | Brooks |
| 3,360,533 A | 12/1967 | Wootton et al. |
| 3,392,002 A | 7/1968 | Hamilton, Jr. et al. |
| 3,607,964 A | 9/1971 | Nalto |
| 3,634,473 A | 1/1972 | Harwood |
| 3,845,087 A | 10/1974 | Maria de Groot |
| 4,032,550 A | 6/1977 | White et al. |
| 4,154,749 A | 5/1979 | Krawack |
| 4,259,294 A | 3/1981 | Van Zijll Langhout et al. |
| 4,268,527 A | 5/1981 | Matsuo et al. |
| 4,275,081 A | 6/1981 | Coleman et al. |
| 4,276,322 A | 6/1981 | Padley et al. |
| 4,284,580 A | 8/1981 | Logan et al. |
| 4,406,777 A | 9/1983 | Melconian |
| 4,414,331 A | 11/1983 | Watanabe et al. |
| 4,416,991 A | 11/1983 | Matsuo et al. |
| 4,420,560 A | 12/1983 | Matsuo et al. |
| 4,472,503 A | 9/1984 | Matsuo et al. |
| 4,502,946 A | 3/1985 | Pronk |
| 4,627,192 A | 12/1986 | Fick |
| 4,629,742 A | 12/1986 | Brady et al. |
| 4,656,045 A | 4/1987 | Bodor et al. |
| 4,735,900 A | 4/1988 | Urata et al. |
| 4,743,402 A | 5/1988 | Fick |
| 4,770,819 A | 9/1988 | Zinnen |
| 4,781,864 A | 11/1988 | Pryor et al. |
| 4,789,528 A | 12/1988 | Owen et al. |
| 4,797,233 A | 1/1989 | Zinnen |
| 4,798,793 A | 1/1989 | Eigtved |
| 4,818,695 A | 4/1989 | Eigtved |
| 4,839,287 A | 6/1989 | Holmberg et al. |
| 4,861,716 A | 8/1989 | Macrae et al. |
| 4,863,860 A | 9/1989 | Halling et al. |
| 4,873,109 A | 10/1989 | Tanaka et al. |
| 4,874,699 A | 10/1989 | Maruzeni et al. |
| 4,880,652 A | 11/1989 | Regutti |
| 4,883,684 A | 11/1989 | Yang |
| 4,935,358 A | 6/1990 | Okada et al. |
| 4,940,845 A | 7/1990 | Hirota et al. |
| 5,010,004 A | 4/1991 | Kosugi et al. |
| 5,032,515 A | 7/1991 | Tanigaki et al. |
| 5,061,498 A | 10/1991 | Narihide |
| 5,089,404 A | 2/1992 | Matsumoto et al. |
| 5,102,582 A | 4/1992 | Zinnen |
| 5,108,916 A | 4/1992 | Cobbs et al. |
| 5,116,745 A | 5/1992 | Mazur et al. |
| 5,124,166 A | 6/1992 | Jacklin et al. |
| 5,128,251 A | 7/1992 | Yokomichi et al. |
| 5,137,660 A | 8/1992 | Mazur et al. |
| 5,142,072 A | 8/1992 | Stipp et al. |
| 5,149,642 A | 9/1992 | Mazur et al. |
| 5,153,126 A | 10/1992 | Schroder et al. |

(Continued)

FOREIGN PATENT DOCUMENTS

| | | |
|---|---|---|
| EP | 0010333 | 4/1980 |
| EP | 0188122 | 7/1986 |

(Continued)

OTHER PUBLICATIONS

Machine translation of JP 07313164 downloaded from the JPO May 18, 2012.*
De Greyt, W. et al., Bioprocessing from the Crop to the Bottle: What to expect from enzymes in future oil processing, 99th OACS Annual Meeting & Expo, Seattle, WA, May 18-21, 2008.
De Greyt, W., Chemical vs. Enzymatic Interesterification, IUPAC-AOCS Workshop on Fats, Oils & Oilseeds Analyses & Production, Tunis, Tunesia, Dec. 6-8, 2004.
Dr. Ir. Marc Kellens, Interesterification, Short Course & Fats Processing, 9th AOCS Conference, Cincinnati, OH, May 8-12, 2004.
Dutton, "The flavor problem of soybean oil IV structure of compounds counteracting the effect of prooxidant metals," The Journal of the American Oil Chemists Society, Nov. 1948, pp. 385-388.
Dutton, "The flavor problem of soybean oil v. some considerations in the use of metal scavengers in commercial operations," The Journal of the American Oil Chemists Society, Aug. 1949, p. 441-444.

(Continued)

Primary Examiner — Susan Hanley
(74) Attorney, Agent, or Firm — Jones Day

(57) ABSTRACT

A method and system for the enzymatic treatment of a lipid containing feedstock comprises contacting the feedstock with a processing aid, then causing the feedstock to pass at a substantially constant flow rate through a treatment system comprising a plurality of enzyme-containing fixed bed reactors connected to one another in series. The fixed bed reactors can be individually serviceable, the flow rate of the feedstock remaining substantially constant through the system when one of the fixed bed reactors is taken offline for servicing. In the most preferred embodiment, the processing aid is a substantially moisture-free silica. The processing aid can be placed in one or more of the fixed bed reactors, disposed above the enzyme in the reactor, or it can be in a pre-treatment system which can comprise one or more reactors.

14 Claims, 6 Drawing Sheets

U.S. PATENT DOCUMENTS

| | | | |
|---|---|---|---|
| 5,166,064 A | 11/1992 | Usui et al. |
| 5,169,670 A | 12/1992 | Yang |
| 5,183,750 A | 2/1993 | Nishide et al. |
| 5,190,868 A | 3/1993 | Kokusho et al. |
| 5,204,251 A | 4/1993 | Kyotani et al. |
| 5,219,733 A | 6/1993 | Myojo et al. |
| 5,219,744 A | 6/1993 | Kurashige et al. |
| 5,225,580 A | 7/1993 | Zinnen |
| 5,264,597 A | 11/1993 | Van Dalen et al. |
| 5,270,188 A | 12/1993 | Yamaguchi et al. |
| 5,288,619 A | 2/1994 | Brown et al. |
| 5,292,649 A | 3/1994 | Kosugi et al. |
| 5,316,927 A | 5/1994 | Zaks et al. |
| 5,336,794 A | 8/1994 | Pryor et al. |
| 5,399,728 A | 3/1995 | Cooper |
| 5,434,278 A | 7/1995 | Pelloso et al. |
| 5,445,955 A | 8/1995 | Ikuta et al. |
| 5,461,170 A | 10/1995 | Miyamoto et al. |
| 5,470,741 A | 11/1995 | Oester et al. |
| 5,480,787 A | 1/1996 | Negishi et al. |
| 5,508,048 A | 4/1996 | Padley |
| 5,569,594 A | 10/1996 | Ikuta et al. |
| 5,591,615 A | 1/1997 | Oester et al. |
| 5,654,181 A | 8/1997 | Oester et al. |
| 5,658,768 A | 8/1997 | Quinlan |
| 5,713,965 A | 2/1998 | Foglia |
| 5,726,048 A | 3/1998 | Oester et al. |
| 5,747,305 A | 5/1998 | Jackson |
| 5,773,266 A | 6/1998 | Bosley et al. |
| 5,849,937 A | 12/1998 | Jubin et al. |
| 5,908,655 A | 6/1999 | Doucet |
| 5,935,828 A | 8/1999 | Zaks et al. |
| 5,945,318 A | 8/1999 | Breivik et al. |
| 5,959,128 A | 9/1999 | Kolstad et al. |
| 5,981,781 A | 11/1999 | Knowlton |
| 6,004,611 A | 12/1999 | Gotoh et al. |
| 6,025,171 A | 2/2000 | Fabian et al. |
| 6,040,161 A | 3/2000 | Cain et al. |
| 6,072,064 A | 6/2000 | Bayense et al. |
| 6,124,486 A | 9/2000 | Cherwin et al. |
| 6,143,348 A | 11/2000 | Cain et al. |
| 6,162,623 A | 12/2000 | Grote et al. |
| 6,238,926 B1 | 5/2001 | Liu et al. |
| 6,258,575 B1 | 7/2001 | Shimizu et al. |
| 6,350,890 B1 | 2/2002 | Kiy et al. |
| 6,361,980 B2 | 3/2002 | Sugiura et al. |
| 6,407,269 B2 | 6/2002 | Kaita et al. |
| 6,566,124 B1 | 5/2003 | Trout et al. |
| 6,605,452 B1 | 8/2003 | Basheer |
| 6,680,396 B2 | 1/2004 | DeBonte et al. |
| 6,689,409 B2 | 2/2004 | DeBonte et al. |
| 6,812,359 B2 | 11/2004 | Goto et al. |
| 6,956,155 B1 | 10/2005 | Martinez-Force et al. |
| 7,081,542 B2 | 7/2006 | Jacobs et al. |
| 7,619,105 B2 | 11/2009 | Green et al. |
| 2003/0054509 A1 | 3/2003 | Lee |
| 2003/0175914 A1 | 9/2003 | Baldenius et al. |
| 2003/0175918 A1 | 9/2003 | Basheer |
| 2004/0166571 A1 | 8/2004 | Sagi et al. |
| 2004/0171127 A1 | 9/2004 | Akimoto et al. |
| 2005/0014237 A1 | 1/2005 | Lee |
| 2005/0233427 A1 | 10/2005 | Schoerken et al. |
| 2006/0057689 A1 | 3/2006 | Otto et al. |
| 2006/0063241 A1 | 3/2006 | Chou |
| 2006/0105438 A1 | 5/2006 | Suzuki et al. |
| 2006/0110807 A1 | 5/2006 | Ohrlein et al. |
| 2006/0115882 A1 | 6/2006 | Negishi et al. |
| 2006/0141592 A1 | 6/2006 | Sumida et al. |
| 2006/0160193 A1 | 7/2006 | Yadav et al. |
| 2006/0257982 A1 | 11/2006 | Binder et al. |

FOREIGN PATENT DOCUMENTS

| | | |
|---|---|---|
| EP | 0307154 | 3/1989 |
| EP | 0378893 | 7/1990 |
| EP | 1004662 | 5/2000 |
| EP | 1094116 | 4/2001 |
| EP | 1111064 | 6/2001 |
| FR | 2772392 | 12/1997 |
| GB | 617078 | 2/1949 |
| GB | 2188057 | 2/1986 |
| JP | 58-126794 | 7/1983 |
| JP | 61-85195 | 4/1986 |
| JP | 61-257192 | 11/1986 |
| JP | 62-81498 | 4/1987 |
| JP | 62-278988 | 12/1987 |
| JP | 63-198992 | 8/1988 |
| JP | 01-120295 | 5/1989 |
| JP | 01-218593 | 8/1989 |
| JP | 02-203789 | 8/1990 |
| JP | 02-203790 | 8/1990 |
| JP | 03-30686 | 2/1991 |
| JP | 04-148690 | 5/1992 |
| JP | 04-330289 | 11/1992 |
| JP | 04-335893 | 11/1992 |
| JP | 05-317064 | 12/1993 |
| JP | 05-328962 | 12/1993 |
| JP | 06-62876 | 3/1994 |
| JP | 07313164 | 12/1995 |
| JP | 08-38190 | 2/1996 |
| JP | 08-140689 | 6/1996 |
| JP | 08-149988 | 6/1996 |
| JP | 08-214890 | 8/1996 |
| JP | 10-215888 | 8/1998 |
| JP | 10-225298 | 8/1998 |
| JP | 11-103884 | 4/1999 |
| JP | 2003-310290 | 11/2003 |
| PT | 0102638 | 3/2002 |
| WO | WO89/01032 | 2/1989 |
| WO | WO92/04360 | 3/1992 |
| WO | WO 99/09119 | 2/1999 |
| WO | WO 99/49070 | 9/1999 |

OTHER PUBLICATIONS

Goderis, H. L., "Lipase-Catalyzed Ester Exchange Reactions in Organic Media with Controlled Humidity," Biotechnology and Bioengineering, Aug. 1987, pp. 257-266, vol. 30.

Kemper, T., Interesterification, An Oil Modification Process, 2004 IOMSA Summer Meeting.

Linfield, Warner, "Enzymatic Fat Hydrolysis and Synthesis," JAOC Proceedings, Feb. 1984, pp. 191-195, vol. 61, No. 2.

Liu et al., "Interesterification of Vegetable Oil Using Immobilized Lipase Fixed Bed Reactors," Zhongguo Nongue Huaxue Huizhi—Journal of the Chinese Agricultural Chemical Society, 1998, vol. 36, No. 2, pp. 134-142, Taipei, Taiwan.

Macrae, A.R., "Enzyme-Catalyzed Modification of Oils and Fats," Phil. Trans. R. Soc. Lond., 1985, pp. 227-233, B310, Great Britain.

"Lipase-Catalyzed Interesterification of Oils and Fats," Philosophical Transactions of the Royal Society of London, Feb. 1983, pp. 291-294, vol. 60, No. 2.

Mensah et al., "Adsorptive Control of Water in Esterification with Immobilized Enzymes. Continuous Operation in a Periodic Counter-Current Reactor," Biotechnology and Bioengineering, 1999, pp. 137-146, vol. 66, No. 3, John Wiley & Sons, Inc., Hoboken, NJ.

Merolli, Alex, "Medium-Chain, Lipids: New Sources, Uses," Inform, Jun. 1997, pp. 597-603, vol. 8, No. 6.

Mill, Carl, "Characteristics of an Immobilized Lipase for the Commercial Synthesis of Esters," JAOCS, Jun. 1988, vol. 65, No. 6.

Nie et al., "Lipase Catalyzed Methanolysis to Produce Biodiesel: Optimization of the Biodiesel Production," Journal of Molecular Catalysis B: Enzymatic, 2006, pp. 142-147, vol. 43, Beijing, China.

Tsujisaka, Yoshiho, "Glyceride Synthesis by Four Kinds of Microbial Lipase," Biochimica et Biophysica Acta, 1977, pp. 915-922, Elsevier/North-Holland Biomedical Press.

"Fats and Oils Processing," Inform, Dec. 1991, pp. 1046-1060, vol. 2 No. 12.

Zhang, Hong, "Production of Margarine Fats by Enzymatic Interesterification with Silica-Granulated Thermomyces Lanuginosa Lipase in a Large-Scale Study," JAOCS, 2001, pp. 57-64, vol. 78, No. 1, AOCS Press.

English Translation of JP 07313164, Human translation; application published Dec. 5, 1995.

* cited by examiner

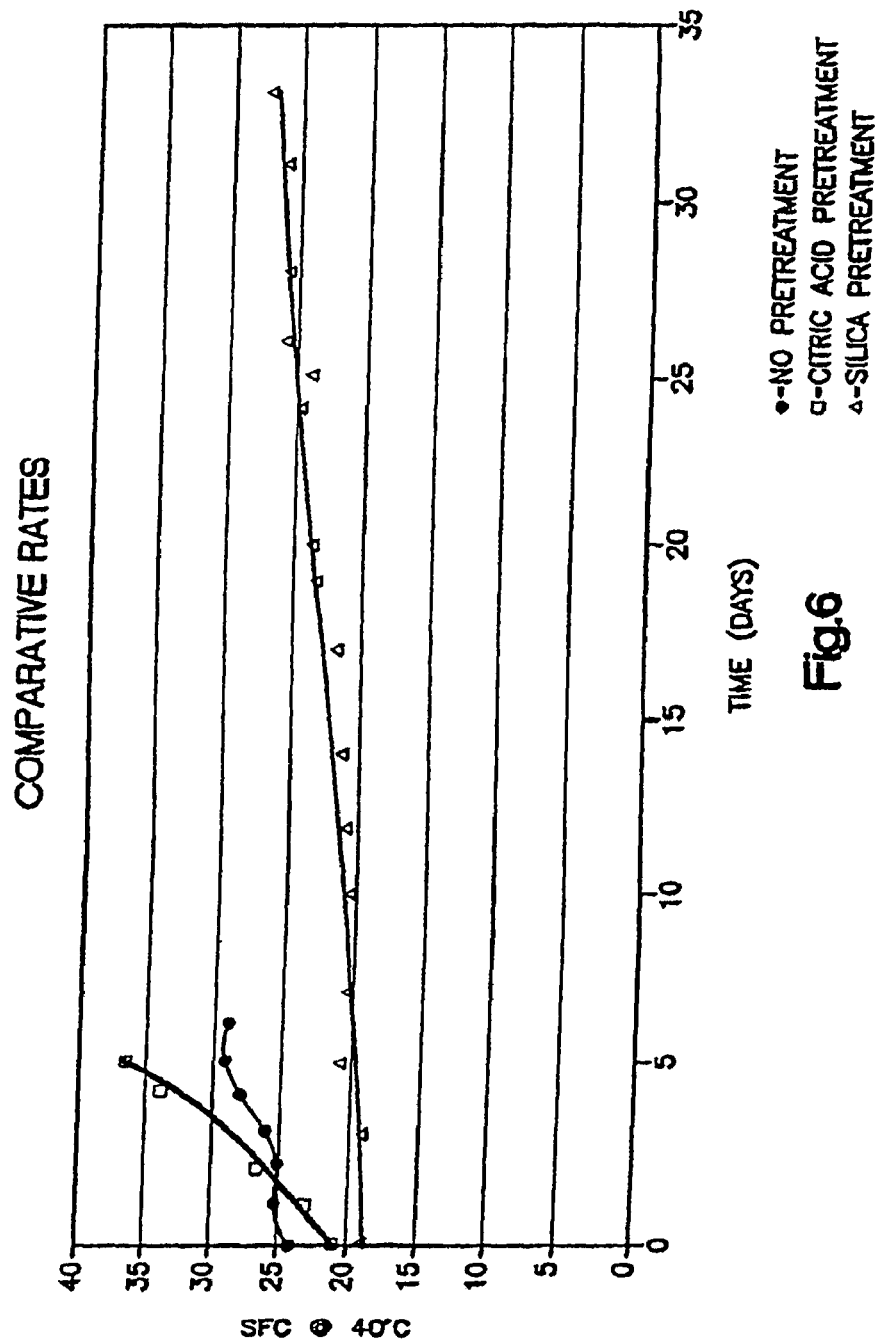

CONTINUOUS PROCESS AND APPARATUS FOR ENZYMATIC TREATMENT OF LIPIDS

RELATED APPLICATIONS

This application is a divisional of U.S. patent application Ser. No. 11/567,318, filed Dec. 6, 2006, entitled "A Continuous Process And Apparatus For Enzymatic Treatment Of Lipids", the disclosure of which is incorporated herein by reference in its entirety.

BACKGROUND OF THE INVENTION

This invention relates to a process for the continuous enzymatic treatment of lipid-containing compositions in a plurality of fixed bed reactors, and to an apparatus for practicing the process. More particularly, this invention relates to a process and apparatus for the continuous enzymatic treatment of lipid-containing compositions using a plurality of fixed bed reactors, wherein the flow of the lipid-containing composition remains substantially constant even as the enzymatic activity of a fixed bed changes over time, and even when a fixed bed is taken off-line such as for repair, replacement, or replenishment. Additionally, this invention relates to a process and apparatus that provides an unexpectedly significant increase in enzymatic activity by pretreating the lipid before it encounters the enzyme and operating the apparatus in a continuous process.

Fats are made of fatty acids attached to a three-carbon glycerol backbone. Fatty acids are made up of chains of carbon atoms with a terminal hydroxyl group. The hydroxyl groups can attach to one, two, or three of the hydroxyl groups on the glycerol backbone to form mono-, di-, or tri-acylglycerols, or fats. The functional and nutritional qualities of the fats will depend on a variety of factors including whether they are monoacylglycerol (MAG), a diacylglycerol (DAG) or a tri-acylglycerol (TAG); the number of carbons in the fatty acid chains; whether the chains are saturated, mono-unsaturated, or poly-unsaturated; whether any unsaturated double bonds in the chains are in the form of the cis or trans isomer; the location of any double bonds along the chains; and the positions of the different types of fatty acids relative to the three carbons of the glycerol backbone.

Lipids are a classification of a broad variety of chemical substances characterized as fats, oils, waxes, and phospholipids. Included within this broad classification are triglycerides, diglycerides, monoglycerides, fatty acids, fatty alcohols, soaps and detergents, terpenes, steroids, and vitamins A, E, $D_2$, and $K_1$. Lipids can be obtained from oilseeds such as soybeans, canola, rapeseed, sunflower, palm, and olives; animal products such as fish, pork, and beef; and synthetic compounds or synthetically derived compositions such as structured lipids for nutritional applications, oleochemicals for industrial and pharmaceutical applications, and biodiesel for energy. Vegetable oils are obtained by pressing or solvent extraction of the oil from the oilseed. The crude oils contain many minor components. Some of these components are detrimental to the performance or aesthetic properties of the oils; others, such as sterols and tocopherols, are nutritionally beneficial.

Lipids obtained from oilseeds (soybean, canola, etc.) by either solvent extraction or mechanical pressing can be refined to remove impurities that may contribute to undesirable colors and/or flavors in the finished product. Traditional refining includes treatment of the oil with sodium hydroxide to neutralize the free fatty acids, and removal of the phospholipids via centrifugation. The oil is then washed with hot softened water and centrifuged to remove the remaining soaps and phospholipids present in the oil. The "once refined" oil is then bleached with "bleaching earth" and filtered to adsorb the chlorophyll and chlorophyll derivatives as well as any remaining soaps, phospholipids, and trace metals present in the oil. The use of bleaching earths or clays for the removal of impurities in lipids is well known in the art. The first common name for the material was "Fuller's earth". Present day bleaching earths may be neutral or acid activated. Mineral clays typically utilized are bentonite, montmorillonite, attapulgite, smectite, and/or hormite.

An alternative process which eliminates the water washing step entirely and replaces it with a treatment of silica gel to adsorb the residual soaps, phospholipids, and trace metals is well known in the art as "Modified Caustic Refining". Pryor et al. U.S. Pat. No. 5,336,794 and Welsh et al U.S. Pat. No. 5,231,201 disclose a two-phase process wherein oil is first contacted with amorphous silica adsorbents to remove all or substantially all soaps or gums or both from the oil and reduce its phospholipid content, and then filtered through a packed bed of a pigment removal agent to decolorize the oil. A silica gel, 0.01 to 1.0 percent, is added to the oil in a slurry after the caustic treated oil is centrifuged. Silica gel products known to be useful for this purpose include those sold under the trademark TriSyl® (silica gel) by W.R. Grace & Co. as amorphous silica free flowing powders containing about 60 to 65 percent moisture with a particle size average of about 18.0 microns minimum, average pore diameter between about 60 and 5000 angstroms, and bulk density of about 500 $kg/m^3$. The oil is mixed with the silica and then dried in a vacuum spray drier; the silica is then filtered out of the oil. If bleaching clay is already on the filter, the process is well known in the art as "Packed Bed Bleaching". The moisture maintains the integrity of the silica pores and allows the impurities to be adsorbed inside the pore.

In recent years there has been increased interest in providing alternatives to the high trans fats and shortening products used in traditional food preparation. Traditionally, liquid oils were manufactured into functional fats containing solids for various margarine and shortening products by nickel hydrogenation. Such hydrogenation processes led to the formation of trans fatty acids. It is believed that fats having reduced trans fatty acids may provide certain health benefits to the consumer. Accordingly, many large food producers are replacing high trans fats with low or even zero trans fats compositions. Originally, efforts at providing low trans fats products focused on reducing the level of hydrogenation of the fat products. More recently, efforts have focused on changing the structure of a liquid oil to change the melting properties and functionality without changing the fatty acid composition or generating trans fatty acids. One method of achieving this is a process known as interesterification.

Interesterification is a known reaction of triacylglycerol structures whereby individual fatty acid structures at positions of the triglyceride being interesterified are interchanged on the glycerol moiety. This is at times referred to or recognized as a randomization wherein fatty acid moieties from one glycerol component of a triacylglycerol are exchanged with those of a glycerol component of another triacylglycerol. This results in triacylglycerol structures which have interchanged fatty acid moieties that vary from glycerol structure to glycerol structure. Art in this area includes Pellosa et al. U.S. Pat. No. 5,434,278, Doucet U.S. Pat. No. 5,908,655, Cherwin et al. U.S. Pat. No. 6,124,486, and Liu et al. U.S. Pat. No. 6,238,926.

The art of interesterification has developed to enable the production of, for example, triglyceride compositions which provide certain melt profiles that can be of interest in certain applications. Generally these are recognized herein as "structured lipids" to distinguish the interesterified products from physical blends of the same components that have not been subjected to interesterification. Swern, *Bailey's Industrial Oil and Fat Products*, $3^{rd}$ edition, pages 941-970 (1964) described the reesterification of fatty acids and glycerol, mono- and poly-hydroxy alcohols, interesterification (acidolysis and alcoholysis), and transesterification of lipids via chemical methods.

Interesterification can be accomplished either chemically or enzymatically. Chemical interesterification is generally accomplished with a chemical catalyst such as sodium methoxide. While chemical interesterification can be less costly in terms of the catalyst, it has several distinct disadvantages. The sodium methoxide catalyst can be dangerous and difficult to handle. The resulting interesterification is random, and does not afford the manufacturer the degree of control that is preferred over the structure of the resulting product. Chemical interesterification also can result in relatively high oil losses. Art in this area includes Kaita et al. U.S. Pat. Application No. 2002/0010359, Bayense et al U.S. Pat. No. 6,072,064, Cooper et al. U.S. Pat. No. 5,399,728, and Stipp et al. U.S. Pat. No. 5,142,072.

In enzymatic interesterification, the enzyme catalyst is more costly than sodium methoxide, and it has low activity and low stability. But enzyme catalysts can afford a great deal of control over the structure of the final interesterified product. In particular the use of certain enzymes can result in interesterification specifically at the 1- and 3-positions along the glycerol backbone chain, exactly where it is most desired. While enzymatic catalysts were originally used only for high value-added products, they are now being used increasingly in the manufacture of commodity fats and fat blends.

Enzymes are complex proteins that produce a specific chemical reaction in other substances without themselves being changed, i.e., a biological catalyst. These biological catalysts are expressed or produced from various microorganisms. Enzymes suitable for use in the present invention include esterase; acylase; those enzymes that facilitate acidolysis reactions, transesterification reactions, ester synthesis, or ester interchange reactions; enzymes having phospholipase or protease activity, including thermostable and thermotolerant hydrolase activity; and polynucleotides. Microorganisms included within the art are *Rhizopus, Aspergillus, Mucor, Geotrichum, Pseudomonas, Penicillium, Chromobacterium, Candida, Achromobacter, Alcaligenes, Corynebacterium, Humicora, Humicolo, Staphylococcus, Rhizomucor, Torulopsis,* and *Bacillus.* Such enzymes produced from the above microorganisms are disclosed by Sugiura et al. U.S. Pat. Application No. 2001/0004462, Bosley et al. U.S. Pat. No. 5,773,266, Quinlan U.S. Pat. No. 5,658,768, Miyamoto et al. U.S. Pat. No. 5,461,170, and Myojo et al. U.S. Pat. No. 5,219,733.

In U.S. Pat. No. 5,508,182, Schneider et al. disclose numerous methods for producing amphiphilic compounds through the biocatalyzed reaction of a hydrophilic substrate, adsorbed onto a solid support, with a second substrate, which may be hydrophobic. Schneider et al. describes methods for producing isomerically pure 1,3-diglycerides and 1-monoglycerides, sugar esters, amino acid esters, peptides, and glycolipids, as well as phosphates of alcohols, carbohydrates, and nucleosides. The patent describes the adsorption of different substrates onto a solid support with an amino-protected amino acid or a carboxyl-protected peptide. Essentially, no reaction occurs without the presence of the substrate adsorbed on the support, examples 1 and 12, thus the support acts as the catalyst for the reactions. All of the examples given were batch reactions, including example 19 where the vinyl-laurate (dissolved in t-BuOMe) is circulated through a packed bed column containing the adsorbed glycerol on the silica gel and the enzyme. The 1,3-dilaurate product is removed from the column by extracting with fresh t-BuOMe. It was not taught or suggested that the glycerol may be re-adsorbed and the reaction operated as a fixed bed reactor independent of the enzyme and/or silica gel. The amount of silica gel utilized in the disclosure ranged from 60 to 1000 percent of the substrate.

Enzymes utilized in the disclosure by Schneider et al. were from *Mucor mihei, Pseudomonas fluoresceins, Rhizopus delemar, Candida cylindracea,* and *Penicillium cyclopium.*

One particularly preferred enzyme catalyst is the lipase from *Thermomyces lanuginosus.* This enzyme is specific for the 1 and 3 sites on the glycerol backbone, and it is heat stable up to about 75° C. This enzyme, however, can be readily inactivated by radicals such as peroxides, certain polar impurities such as phosphatides and soaps, secondary oxidation products such as ketones and aldehydes, and trace metals. Thus, the quality of the oil feedstock is important. U.S. Patent Publication No. 2003/0054509 discloses the pretreatment of an oil prior to enzymatic interesterification with a silica. The amount of silica utilized in the examples was 172 percent of the enzyme utilized for the reaction (38 g of silica per 22 g of enzymes)

An immobilized granulated form of the lipase from *Thermomyces lanuginosus* is sold by Novozymes Corporation under the registered trademark Lipozyme®TL IM. The product literature that comes with this enzyme product discloses a process of use comprising cooling the lipids to 70° C., pumping the lipids to a single reactor column or tank, and passing the oil through the column or mixing the oil with the enzyme in the tank. The lipids contact the enzyme in the column or tank and are continuously interesterified. The interesterified lipids may then be blended with other lipids, or deodorized, or shipped to the final customer.

Factors to be considered in designing an enzymatic interesterification process include whether it should be batch or continuous, whether it will include a single or multiple fixed bed reactor, if multiple fixed beds, whether the beds will be in series or in parallel, whether the flow rate will be variable or constant, how to control the extent of enzymatic conversions, and problems with potential cross-contamination. See e.g., "Chemical vs. Enzymatic Interesterification," by Wim De Greyt of the DeSmet Group, Belgium, presented at the IUPAC-AOCS Workshop on Fats, Oils and Oilseeds Analyses and Production, Dec. 6-8, 2004, available at http://www.aocs.org/archives/analysis/pdfs/degreyt-interesterification-modifieddgw.pdf. As disclosed therein, if a single fixed bed reactor is used, the enzymatic activity will decrease over time. The flow rate must be decreased in order to ensure that the reaction is allowed to go to completion. This requires a variable speed control pump, as well as regular monitoring of the conversion, and results in a low production rate at the end of the enzyme's lifetime. The process cannot be operated continuously because of the frequent need to remove and replace enzymes in the column. Often a catalyst bed must be replaced even if some of the catalyst in the bed is still active, resulting in waste of active catalyst. The size of the enzyme bed column is limited, because if the height is too great, the enzyme granules at the bottom may be crushed under the pressure exerted by the system pump, and if the diameter is too great, the granular material may distribute so as to form channels through which oil may pass without contacting and thereby-reacting with the enzyme.

In a multiple fixed bed series reactor system, each fixed bed will have a different enzyme activity, with the first reactor bed having the lowest enzyme activity, and the last reactor having the highest enzyme activity. This is because the first reactor in the series absorbs more of the impurities and harmful components, thereby protecting the more active enzyme in the further reactors. Owen et al. disclose in U.S. Pat. No. 4,789,528 the operation of a sequential rotation of reactors in a multi-reactor fixed bed system utilizing zeolites in a petrochemical application to produce a variety of refined petrochemical products.

U.S. Pat. Publication No. US 2005/0014237 discloses a method of enzymatic interesterification wherein the feedstock is deodorized prior to contact with an enzyme, for the purpose of prolonging the half-life of the enzyme. Deodorization is described therein as typically the last step in the conventional oil refining process, and as being principally a steam distillation, during which substances with greater volatility are removed by high temperature under vacuum. Various substances removed by deodorization include free fatty acids and various flavor and odor compounds either present originally or generated by oxidation of fats and oils. Also removed are the substances formed by the heat decomposition of peroxides and pigments.

As reported by Ten Brink et al. in US 2005/0019316, JP 08000275 discloses that a pre-treatment of 2 percent acid activated bleaching clay for 20 minutes at 110° Celsius increases the enzyme's half life. Ten Brink et al. in U.S. Pat. Application No. 2005/0019316 further report, however, that such prior attempts to prolong the half life of a catalyst by purification of the lipids have been realized only on small scale laboratory processes, and that such processes have always failed when upgraded to an industrial scale. To address this concern, Ten Brink et al. disclose a method of treating "bleached" glyceride fats with a "bleaching earth zeolite" under high shear energy of 0.5 to 2.5 W/kg for a duration ranging from 5 minutes to 12 hours at a temperature range of 30 to 150° Celsius before exposing the lipid to a lipase catalyst for interesterification.

Other enzymatic treatments of lipid compositions are known. In addition to a lipase, enzymes of interest can include esterase; acylase; those enzymes that facilitate acidolysis reactions, transesterification reactions, ester synthesis, or ester interchange reactions; enzymes having phospholipase or protease activity, including thermostable and thermotolerant hydrolase activity; and polynucleotides.

It is thus an object of the invention to provide a process and apparatus for the continuous enzymatic treatment of a lipid-containing composition in multiple reaction modules connected in series, wherein the process can proceed continuously even if one of the modules has to be taken off-line for replacement of replenishment of the treatment medium.

It is thus another object of the invention to provide a process and apparatus for the continuous enzymatic treatment of a lipid-containing composition, in which the activity of the enzymes is prolonged.

It is another object of the invention to provide a process and apparatus for the continuous enzymatic treatment of a lipid-containing composition in multiple fixed bed reactors connected in series, wherein a fixed bed reactor can be replaced or replenished while the process remains at a substantially constant flow rate.

It is yet another object of the invention to provide a process and apparatus for continuous enzymatic treatment of a lipid-containing composition in multiple fixed bed reactors connected in series, wherein substantially all of the activity of a quantity of enzyme can be utilized before that quantity of enzyme is replaced or replenished.

It is yet another object of the invention to provide a process and apparatus for the enzymatic treatment of a lipid-containing composition in which the composition does not have to be deodorized prior to enzymatic treatment.

It is yet another object of the invention to provide a process and apparatus for the enzymatic treatment of a lipid-containing composition which requires only limited monitoring of the treatment process.

It is yet another object of the invention to provide a process and apparatus for the enzymatic treatment of a lipid-containing composition that is capable of producing a lipid-containing product meeting predetermined product specifications.

It is yet another object of the invention to provide a process and apparatus for the enzymatic treatment of a lipid-containing composition in multiple fixed bed reactors connected in series in which the flow rate remains substantially constant and is capable of producing a lipid-containing product meeting predetermined product specifications.

SUMMARY OF THE INVENTION

The present invention relates to a process and apparatus for the continuous enzymatic treatment of lipid-containing compositions using a plurality of fixed bed reactors, wherein the flow of the lipid-containing composition through the apparatus can remain substantially constant even as the enzymatic activity of a fixed bed decreases over time, and even when a fixed bed is taken off-line such as for repair, replacement, or replenishment. In accordance with this aspect of the invention, a method for the continuous treatment of a composition comprises the steps of (a) providing a lipid-containing feedstock, (b) pre-treating said feedstock with a first processing aid to pre-treat the feedstock, (c) causing said feedstock to pass at a substantially constant flow rate through a treatment system comprising a plurality of enzyme-containing fixed bed reactors connected to one another in series, and (d) said fixed bed reactors being individually serviceable, the flow rate of the feedstock remaining substantially constant through the treatment system when one of said fixed bed reactors is taken off line for servicing.

In one embodiment of the invention, the processing aid can be placed within each fixed bed reactor, positioned above the enzyme bed so that the feedstock that flows into the reactor first contacts the processing aid, and then the enzyme. In another embodiment, the processing aid can be in one or more reactors that are distinct from the reactors that hold the enzyme. Thus, in another aspect of the invention, a pre-treatment system for pre-treating the feedstock can include one or more pre-treatment reactors, each pre-treatment reactor containing a pre-treatment processing aid suitable for the particular lipid-containing composition to be treated, typically silica. In accordance with this aspect of the invention, the method of the present invention can comprise the steps of (a) providing a lipid-containing feedstock composition, (b) contacting the lipid-containing feedstock composition with a quantity of a pretreatment processing aid in a pretreatment system for a period of time sufficient to provide a pretreated feedstock, the pretreatment system comprising a plurality of pre-treatment reactors connected in series, (c) causing said feedstock to pass at a substantially constant flow rate through a treatment system comprising a plurality of enzyme-containing fixed bed reactors connected to one another in series, and (d) the pre-treatment reactors being individually serviceable, the flow rate of the feedstock remaining substantially constant through the remaining pre-treatment system when one of said pre-treatment reactors is taken offline for servicing.

In yet another aspect of the invention, the inventors herein further have found that the activity of the enzyme catalysts is greatly prolonged if the silica used in the pre-treatment step is substantially moisture free. This is in contrast to silica products attempted to be used in pre-treatment processes of the prior art, such silica products having moisture contents approaching 65%. Thus in another aspect of the invention, the method of the present invention comprises the steps of (a) providing a lipid-containing feedstock composition, (b) contacting the lipid-containing feedstock composition with a quantity of substantially moisture-free silica to provide a pre-treated feedstock, (c) causing said feedstock to pass at a substantially constant flow rate through a treatment system comprising one or more enzyme-containing fixed bed reactors connected in series.

In a preferred embodiment of this aspect of the invention, the treatment system comprises a plurality of fixed bed reactors that are individually serviceable, the flow rate of the feedstock remaining substantially constant through the treatment system when one of said fixed bed reactors is taken offline for servicing.

In some embodiments, the feedstock can comprise one or more lipid-containing compositions that preferably are either refined and bleached; refined, bleached, and hydrogenated; or fractionated, refined, and bleached. The pre-treatment system of the present invention can serve to remove undesirable components of the feedstock, whether those components are known or unknown. The enzyme in the treatment system is immobilized in the fixed bed reactors and can be a lipase; esterase; acylase; those enzymes that facilitate acidolysis reactions, transesterification reactions, ester synthesis, or ester interchange reactions; enzymes having phospholipase or protease activity, including thermostable and thermotolerant hydrolase activity; and polynucleotides.

In another aspect, the invention relates to an apparatus for carrying out the method as set forth above, the apparatus comprising (a) a feedstock inlet, (b) a product outlet, (c) a pretreatment system comprising one or more treatment modules, (d) a treatment system comprising a plurality of enzyme containing fixed bed reactors connected in series, and (e) an adjustable fluid communication means that allows feedstock to flow into the apparatus through the inlet, through the pre-treatment system, through the treatment system, and out of the apparatus through said outlet, the fluid communication means being adjustable so as to allow one of the pre-treatment modules and/or fixed bed reactors to be taken off line while the feedstock continues to flow through the apparatus, whereby a module or reactor can be taken off line while the flow of the feedstock composition through the apparatus remains substantially constant. In a preferred embodiment, the pretreatment system comprises an amount of substantially moisture-free silica disposed within said one or more pre-treatment modules. In a more preferred embodiment, the pre-treatment modules are in the form of fixed-bed reactors.

Because a pre-treatment module or fixed bed reactor can be taken off-line while the process is in operation, the process need not experience the slow-downs and stoppages that occur in prior art systems when an enzyme bed gradually loses its activity. A significant advantage of the method and apparatus of the present invention is that the rate of reaction will not decrease substantially as the reaction proceeds, so that it is not necessary to decrease the rate of flow of feedstock into the apparatus, and the method and apparatus can operate at a substantially constant flow rate, even when a treatment module is being replenished or replaced. The process and apparatus of the present invention provide significantly prolonged enzyme activity, and allow use of substantially all the enzymatic activity in a reactor before the reactor is taken off line for replenishment. The process and apparatus of the invention also allow the treatment to proceed with less operator monitoring of the process than is necessary with single module treatment methods. Yet another advantage is that it is possible to produce a treated product that meets predetermined product specifications. Yet another advantage of the invention is that high quality products can be achieved without deodorizing the lipid-containing composition prior to the pre-treatment and enzyme treatment steps.

DESCRIPTION OF THE FIGURES

FIG. 6 is a graph comparing the change in the 40° Solid Fat Content of three trials of an oil product that has been subjected to the pre-treatment and treatment processes in accordance with the present invention against the number of days of conducted in the trials.

DETAILED DESCRIPTION OF THE INVENTION

Figure 1:
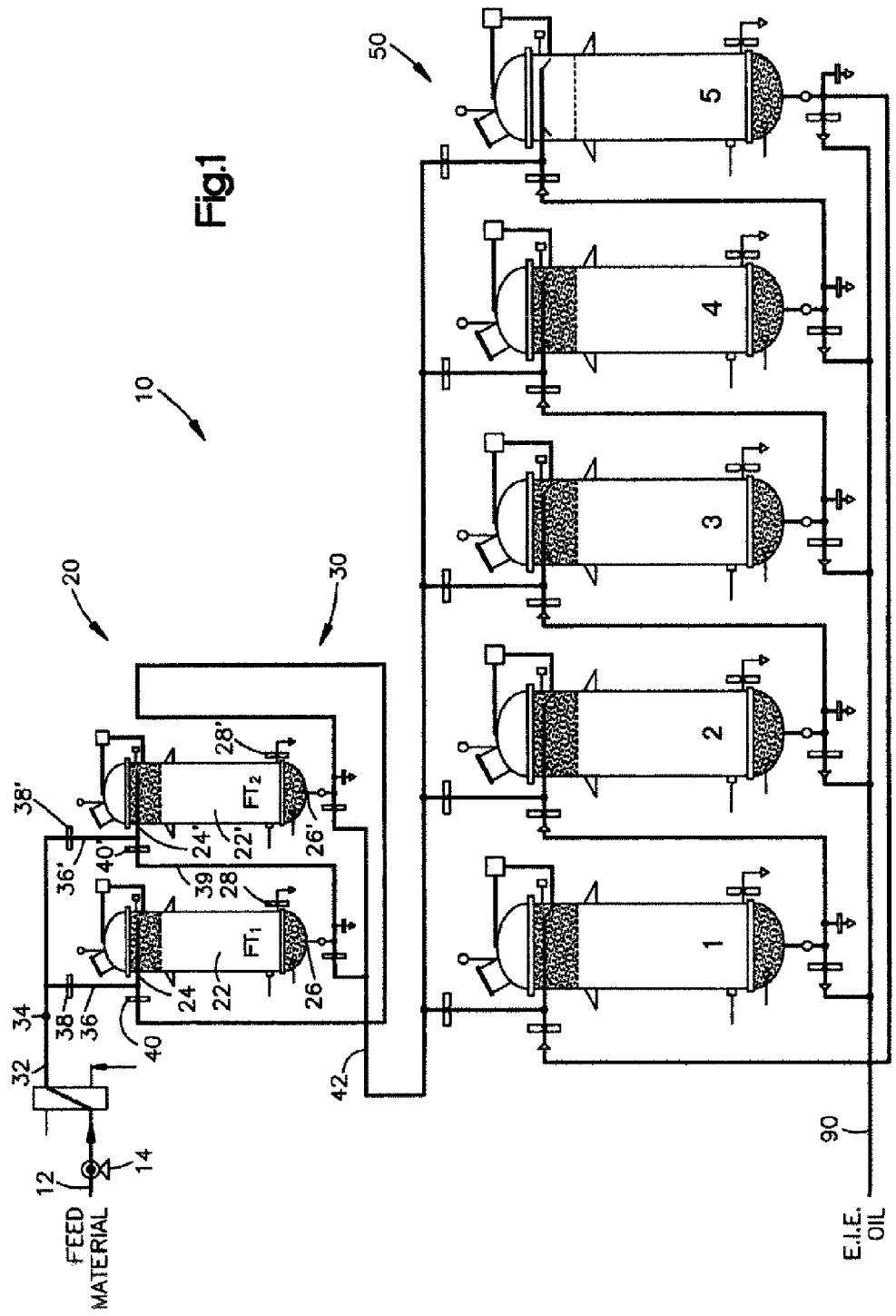
FIG. 1 is a schematic view of one embodiment of an apparatus that can be used in the practice of the method of the present invention, the apparatus comprising a pre-treatment system and a treatment system.

As required, a detailed description of an embodiment of the invention is disclosed herein. It is to be understood, however, that the disclosed embodiment is merely exemplary of the invention, which may be embodied in various forms. Therefore, specific details as disclosed herein are not to be interpreted as limiting, but merely as a basis for the claims and as a representative basis for teaching one skilled in the art to variously employ the many aspects of the present invention in any appropriate manner.

The present invention relates to a process and apparatus for treating a lipid-containing feedstock. The feedstock can comprise one or more lipid-containing compositions that preferably are either refined and bleached; refined, bleached, and either fully or partially hydrogenated; or fractionated, refined, and bleached. Such compositions can comprise fats or oils from either vegetable sources or animal sources. If from vegetable sources, the oil or fat can be obtained by mechanical pressing or chemical extraction. Oils and fats suitable for use in the lipid-containing composition include, for example and without limitation, canola oil, castor oil, coconut oil, coriander oil, corn oil, cottonseed oil, hazelnut oil, hempseed oil, linseed oil, meadowfoam oil, olive oil, palm oil, palm kernel oil, peanut oil, rapeseed oil, rice bran oil, safflower oil, sasanqua oil, soybean oil, sunflower seed oil, tall oil, tsubaki oil, varieties of "natural" oils having altered fatty acid compositions via Genetically Modified Organisms (GMO) or traditional "breeding" such as high oleic or low linolenic, low saturated oils (high oleic canola oil, low linolenic soybean oil or high stearic sunflower oils), vegetable oil, menhaden, candlefish oil, cod-liver oil, orange roughly oil, sardine oil, herring oils, lard, tallow, and blends of any of the above.

Silica products used in the pre-treatment step of the present invention are preferably substantially moisture-free. By "substantially moisture free" it is meant that the silica product has less than about 10% volatiles, and more preferably less than about 5% volatiles. Preferably when analyzed on a dry basis, the product is at least about 95% $SiO_2$, and preferably at least about 99% $SiO_2$. In addition, the silica product can have an average pore size of greater than about 150 Angstroms, preferably greater than about 160 Angstroms. To avoid the formation of soaps in the reactor, it is preferred that the silica have a pH of less than about 7.0, and a pH of about 6.8 is particularly preferred. It has been found that the use of such silica in a pre-treatment step unexpectedly prolongs the useful life of the enzyme catalyst in a lipid treating system. The silica processing aid can comprise a silica product selected from one or more of the group consisting of chromatographic silica, fused silica, precipitated silica, fumed silica, colloidal silica, amorphous silica, silica hydrogel, and sodium aluminum silicate. Chromatographic grade silica has been found to be suitable in the method and apparatus of the present invention. One product known to be particularly suited for use in a pretreatment system of the present invention is a substantially moisture-free silica gel product provided by W.R. Grace & Co. under the product designation SP 535-10065. It has been found that when a substantially moisture-free silica product is used, the amount of silica used per amount of enzyme can be about 50% or less, and preferably about 25% or less, and most preferably about 15% or less.

The enzymes used in the process and apparatus of the present invention are immobilized enzymes in fixed bed reactors and can be a lipase; esterase; acylase; those enzymes that facilitate acidolysis reactions, transesterification reactions, ester synthesis, or ester interchange reactions; enzymes having phospholipase or protease activity, including thermostable and thermotolerant hydrolase activity; and polynucleotides. Suitable enzymes include, without limitation, those derived from of *Achromobacter, Alcaligenes, Aspergillus, Bacillus, Candida, Chromobacterium, Corynebacterium, Geotrichum, Humicolo, Humicora, Mucor, Penicillium, Pseudomonas, Rhizomucor, Rhizopus, Staphylococcus, Thermomyces*, and *Torulopsis*. Suitable derived enzymes include without limitation *Mucor mihei, Pseudomonas fluorescens, Rhizopus delemar, Candida cylindracea, Penicillium cyclopium*, and *Thermomyces lanuginosus*. A particularly preferred enzyme catalyst is the lipase from *Thermomyces lanuginosus*.

Productivity of an enzyme treatment system for fats or oils can be evaluated in terms of kilograms of oil successfully treated per gram of enzyme in the treatment system. Successful treatment of an oil or fat means that the treated oil or fat comes within product specifications for the product sought to be achieved with the enzymatic treatment. When a quantity of enzyme becomes deactivated, it will no longer successfully treat the oil or fat with which it comes in contact. In the method and apparatus of the present invention, the enzyme can process much more fat or oil than the same enzyme in prior art processes, even if the fat or oil has not been deodorized prior to treatment in the inventive process. In accordance with the present invention, the activity of the enzyme is at least about 1.0 kg oil/g enzyme, more preferably at least about 1.5 kg oil/g enzyme, and most preferably at least about 1.8 kg oil/g/enzyme.

The process of the present invention may produce better results when operated under conditions of controlled pH. Generally, the pH should be less than about 7.2. Good results are expected when the pH is in the range of about 3-7, and the preferred pH can be about 6.8.

In the Figures, like reference numerals are used to refer to like parts.

Referring now to FIG. 1, an embodiment of an apparatus 10 for use in the method of the present invention comprises a feedstock inlet 12, a pretreatment system 20, a treatment system 50, and a product outlet 90. In the illustrated embodiment, each of the pre-treatment system 20 and the treatment system 50 comprises a plurality of modules or reactors connected to one another in series. It will be appreciated, however, that not all embodiments of the invention will include a pre-treatment system. Further, where a pre-treatment system is included, the system comprising a plurality of modules or reactors can be in either the pre-treatment system, or the treatment system, or both.

Figure 2:
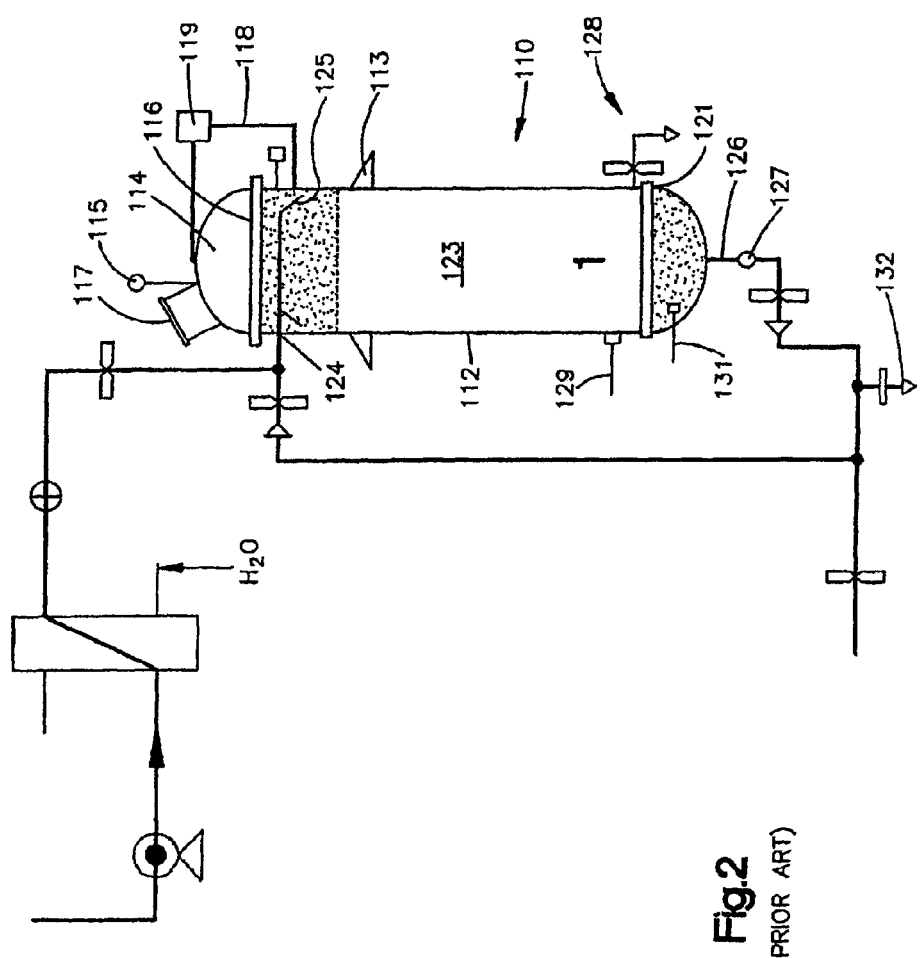
FIG. 2 is a schematic view of one embodiment of a fixed bed reactor of the prior art that can be used as a treatment module in the method and apparatus of the present invention.

FIG. 2 illustrates a typical fixed bed reactor of the prior art that can be used as a pre-treatment or treatment module in the apparatus of the present invention. Each fixed bed reactor comprises a reactor housing 110 which contains a pre-treatment or treatment medium 123 that rests on a retaining means 121, such as a wire screen or other permeable means that retains the treatment medium while allowing flow-through of the feedstock being treated. Reactor housing 110 can comprise a body portion 112 and a cap portion 114 that are sealingly engaged at gasket 116. Cap portion 114 can be released from body portion 112 by means of mechanical arm 118 having a hinge 119. Cap portion 114 is provided with pressure gauge 115 and sight glass 117, which allow conditions within the reactor housing 110 to be monitored. Body portion 112 can be provided with mounting brackets 113, inlet 124, outlet 126, and secondary cleaning port 128. Disposed below outlet 126 is sight glass 127. Disposed within the interior of body portion 110 is an umbrella-shaped feedstock flow distribution system 125, known colloquially in the industry as a "chinaman's hat." Body portion 112 further can be provided with a temperature probe 129 disposed above retaining means 121 and temperature probe 131 disposed below retaining means 121. Sampling port 132 advantageously can be located downstream of outlet 126. It will be appreciated that the design of the particular reactor or treatment module is not itself a critical aspect of the present invention, and that treatment modules or reactors of other structure or design could be used in the practice of the present invention. The foregoing description of one possible reactor design is provided to facilitate understanding of the description of the invention.

Figure 3:
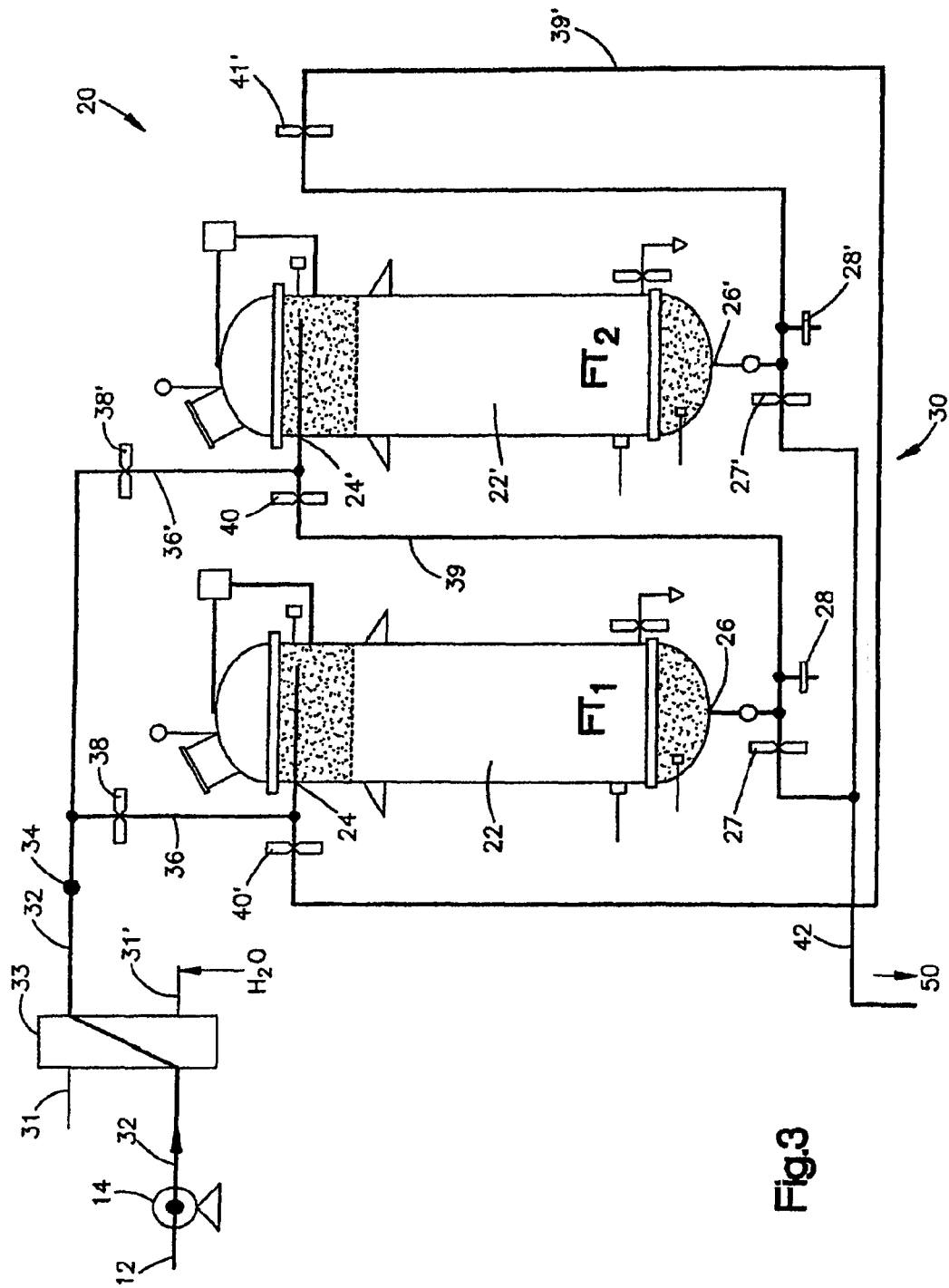
FIG. 3 is an enlarged view of the pre-treatment system of FIG. 1.

When pretreatment of a feedstock is desired, a suitable pre-treatment system can comprise either a single module or a plurality of modules. Each such module can be in the form of a fixed bed reactor as illustrated in FIG. 2, or it can be in a different embodiment as may be most suitable for a particular situation. FIG. 3 illustrates an embodiment of such a pre-treatment system of the present invention, in which a plurality of pre-treatment modules is used, each pre-treatment module being in the form of a fixed bed reactor substantially as illustrated in FIG. 2. In the illustrated embodiment, pretreatment system 20 comprises fixed bed reactors 22 and 22', and an adjustable fluid communication means 30, which communication means 30 comprises the system of fluid conduits into, out of, and between reactors 22 and 22', including appropriate valves and meters, as explained more fully below. Each fixed bed reactor comprises an inlet port 24, 24' and an outlet port 26, 26'. Associated with each outlet port 26, 26' is an output flow shut-off valve 27, 27'. Each reactor bed is packed with a suitable pretreatment medium, not shown. In a preferred embodiment, the pre-treatment medium is a substantially moisture-free silica. Adjustable fluid communication means 30 comprises a conduit 32 leading from inlet 12. Downstream of inlet 12 is pump 14 that maintains a substantially constant flow of feedstock into conduit 32. Conduit 32 passes through heat exchanger 33 with heat exchange medium inlet and outlets 31, 31'; the heat exchanger can be used to maintain an optimum temperature of the inflowing feedstock for a specific pre-treatment medium. Water is one acceptable heat exchange medium. Conduit 32 is provided with a flow transmitter 34, which monitors the flow-rate of the feedstock, and connectors 36 and 36' leading into inlet ports 24, 24' of reactors 22 and 22', respectively. Each connector 36, 36' is provided with a shut-off valve 38, 38'. Reactors 22 and 22' are connected to one another in series via primary inter-reactor connector 39 having shut-off valve 40, and extending from outlet 26 of reactor 22 to inlet 24' of reactor 22'. Reactors 22 and 22' also are connected to one another in series via secondary inter-reactor connector 39' having shut-off valves 40' and 41' and extending from outlet 26' of reactor 22' through shut-off valves 41' and 40' to inlet 24 of reactor 22.

In normal operation, fluid communication means 30 is initially set with shut-off valves 38, 40, and 27' in the open position, and shut-off valves 38', 40', 27, and 41' in the closed position. In initial operation, feedstock flows from inlet 12 into conduit 32 via pump 14 and through heat exchanger 33, then through flow transmitter 34. As shut-off valves 38' and 40' are closed, all the feedstock will flow through open shut-off valve 38 into connector 36, through inlet port 24 and then into reactor 22 where it meets the first pretreatment fixed bed. The feedstock travels out through outlet 26. Since output valve 27 is closed, the feedstock then travels through primary inter-reactor connector 39 and via open valve 40 to inlet 24', and then into reactor 22' where it meets the second pretreatment bed. The fully pre-treated feedstock then flows out through outlet 26', then through open valve 27'. At this point the output of reactor 22' is completely pretreated, and the pretreated feedstock can flow through conduit 42 to treatment system 50.

It will be appreciated that the pretreatment medium in reactor 22 initially will encounter significantly more impurities than the pretreatment medium in reactor 22', such that reactor 22 will become depleted before reactor 22'. Sample ports 28, 28' on each of reactors 22, 22' allow the operator to sample the pre-treated composition at the end of the reactor to determine the functionality of the pretreatment medium in the reactor. In systems of the prior art, the output of the reactors would have to be monitored frequently to determine if the functionality of the medium was decreasing. When such a condition occurred, the rate of treatment in reactor 22 would decrease, so that the rate of input of feedstock through pump 14 as measured by flow transmitter 34 would have to be decreased. Eventually, the entire system would have to be shut down and the contents of the one or more reactors replaced with fresh pre-treatment medium, even if not all the medium in the bed or beds had been deactivated.

These disadvantages of the prior art are overcome by the method and apparatus of the present invention. In accordance with the invention, if it is determined that the pre-treatment medium of reactor 22 needs to be replaced, the following procedure is followed. Shut-off valves 38 and 40 are closed, and shut off valves 38' is opened. In this configuration, feedstock no longer flows into conduit 36 and reactor 22, but instead flows through conduit 36' into reactor 22'. Because valve 40' Is closed, feedstock cannot flow back through primary inter-reactor connector 39. Reactor 22' is now the first pre-treatment reactor. The feedstock travels out of reactor 22' through outlet 26', then through valve 27' to conduit 42 and out to treatment system 50.

At this point in the process, reactor 22 is "off-line," which is to say that no feedstock is flowing either into or out of reactor 22. Reactor 22 can be opened and the "spent" pre-treatment material replaced, or reactor 22 can undergo other maintenance and service procedures. Once service of reactor 22 is complete it can be brought back on-line. Valve 27' is closed and valves 41', 40' and 27 are all opened, allowing the feedstock to flow from reactor 22' through valve 41' continuing through secondary inter-reactor connector 39', and then through valve 40' and into inlet 24 allowing the feedstock to encounter new pretreatment material in reactor 22. Reactor 22 is now the second pretreatment reactor. The pretreated feedstock now travels through outlet 26, then through valve 27 and through conduit 42 to treatment system 50.

Figure 4:
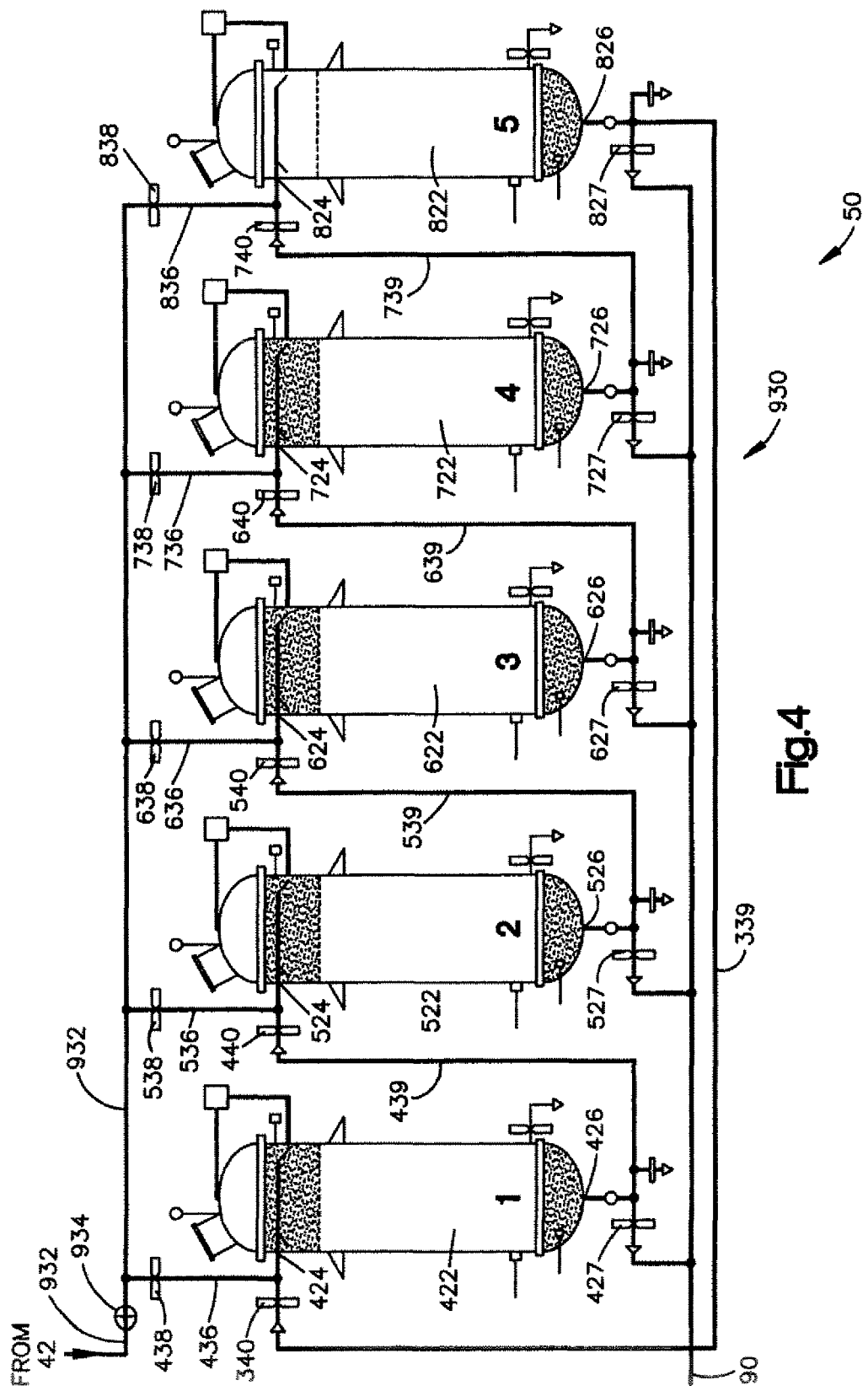
FIG. 4 is an enlarged view of the treatment system of FIG. 1.

The same principles illustrated and described above with respect to a two-module pre-treatment system also can be applied to a multiple-fixed bed reactor treatment system as illustrated in FIG. 4. In the illustrated embodiment there are five treatment modules 422, 522, 622, 722, and 822 in the form of fixed bed reactors, each bed including an immobilized enzyme suitable for treating a lipid-containing composition. Each fixed bed reactor comprises an inlet port 424, 524, 624, 724, and 824, and an outlet port 426, 526, 626, 726, and 826. Associated with each outlet port is an output flow shut-off valve 427, 527, 627, 727, and 827. Adjustable fluid communication means 930 comprises the system of fluid conduits into, out of, and between reactors 422, 522, 622, 722, and 822, with valves and meters, as explained more fully below. Conduit 932 leads from conduit 42 of pre-treatment system 20. Conduit 932 is provided with a flow transmitter 934, which monitors the flow rate of the pre-treated feedstock. Connectors 436, 536, 636, 736, 836 lead into inlet ports 424, 524, 624, 724, and 824 of reactors 422, 522, 622, 722, 822 respectively. Each connector is provided with a shut-off valve 438, 538, 638, 738, 838. The reactors are connected to one another in series via primary inter-reactor connectors 439, 539, 639, 739 having shut-off valves 440, 540, 640 and 740. The reactors also are connected to one another in series via secondary inter-reactor connector 339 having shut-off valve 340.

In normal initial operation, valves 438, 440, 540, 640, 740, and 827 are all open, and the remaining valves are closed. Pre-treated feedstock flows from conduit 42 into conduit 932, through flow transmitter 934, and through open valve 438. As shut-off valves 340, 538, 638, 738, and 838 are all closed, all the feedstock will flow through open shut-off valve 438 into connector 436, through inlet port 424 and then into reactor 422 where it contacts the first treatment fixed bed. The feedstock travels out through outlet 426. Since output valve 427 is closed, the feedstock then travels through primary inter-reactor connector 439 and via open valve 440 to inlet 524, and into reactor 522 where it meets the second treatment bed. In the same manner, the flow of feedstock continues on through reactors 622, 722, and 822. At this point the output of reactor 822 is completely treated, and the treated lipid composition can flow through conduit 90 and out of the apparatus.

Analogous to pre-treatment system 20, the first treatment module in the series of treatment system 50 will be the first to show a decrease in enzymatic activity, and eventually will need to be replaced. The following description will apply with respect to taking first reactor 422 off-line for service such as replenishment of enzyme, however the description will be equally applicable to taking any of the other reactors offline, with reference to the corresponding parts. In accordance with the invention, if it is determined that the fixed bed reactor 422 needs to be serviced, the following procedure is followed. Shut-off valves 438 and 440 are closed, and shut off valves 538 is opened. In this configuration, feedstock no longer flows into conduit 436 and reactor 422, but instead flows through conduit 536 into reactor 522. Because valve 440 is closed, feedstock cannot flow back through primary inter-reactor connector 439. Reactor 522 is now the first treatment bed. The feedstock travels out of reactor 522 through outlet 526, then continues through reactors 622, 722, and 822 in the same manner and out of treatment system 50 via conduit 90.

At this point in the process, reactor 422 is "off-line," which is to say that no feedstock is flowing either into or out of reactor 422. Reactor 422 can be opened and the "spent" treatment material replaced, or reactor 422 can undergo other maintenance and service procedures. Once servicing of reactor 422 is complete it can be brought back on-line. Valve 827 is closed and valves 340 and 427 are opened, allowing the feedstock to flow from reactor 822 through outlet 826 into secondary inter-reactor connector 339, and then through valve 340 and into inlet 424 allowing the feedstock to encounter new treatment material in reactor 422. Reactor 422 is now the last treatment bed. The fully treated feedstock now travels through outlet 426, then valve 427 and through conduit 90 to exit treatment system 50.

In the same manner, when it is time to change reactor 522, it will be taken offline in the same manner, reactor 622 will become the first reactor in the series, reactor 522 will be serviced, and will be brought back on-line as the last reactor in the series. This process can be repeated for each of the reactors as the enzyme beds gradually lose their functionality. It will be seen that the freshest bed is always brought back on line as the last in the series, thus receiving the lipid composition after it has already gone through all of the remaining reactors. The composition when it reaches the last reactor in the series has already been extensively treated, and is relatively free of any impurities due to either removal or reaction with the previous enzyme in each of the prior reactors, insuring substantially complete reaction of the composition. The enzyme in the last reactor in the series retains its functionality far longer than when the same reactor was the first in the series. Further, more of the enzyme in the reactor is used before the reactor has to be taken offline again. Surprisingly, it has been found that as much as a six-fold increase in useful life of an enzyme reactor bed can be achieved with the method and apparatus of the present invention as compared to prior art systems.

The method and apparatus of the present invention provide significant advantages over prior art methods and apparatus for enzyme treatment of lipid compositions. Catalyst life can be increased as much as six-fold. The pre-treatment with silica or other pre-treatment medium is continuous without any interruption due to deactivation or replacement of the pre-treatment medium in a particular pre-treatment module. Similarly, the modification of the lipids is continuous without any interruption due to enzyme de-activation or replacement of the immobilized enzymes. The flow rate is not only continuous but also substantially constant. Substantially 100 percent conversion of a lipid composition can be achieved without any interruption or process flow rate changes. Limited process monitoring is required to ensure substantially 100 percent conversion. Moreover, good quality products can be achieved without the requirement of a deodorization step prior to or during silica pre-treatment or enzymatic treatment.

The following examples set forth the development of the method of the present invention, including the verification of the steps of the invention and comparisons with other processes. To the extent the examples relate to the invention as claimed herein, the examples are presented by way of illustration and not by way of limitation, and are intended to illustrate but a few of the many possible ways in which the present invention can be practiced.

Example 1

Verification of Enzymatic Interesterification

Control

The oil used in each of the following examples was a blend of fully hydrogenated refined and bleached oil produced from Palm Kernel (PK) and Palm Oils (PO) (60:40 blend), utilized as the hard stock for a "zero" trans type margarine product having "zero" trans-fatty acids, and brought to liquid temperature and bleached with 1% bleaching earth and 0.5% of TrySil® silica in accordance with known methods. The vacuum was broken with nitrogen and the resulting material was stored at less than 10° Celsius until used in the various examples herein.

In the initial verification of enzymatic interesterification, samples of the oil blend were interesterified without any pre-treatment utilizing both the traditional CIE (chemical interesterification) method with sodium methoxide catalyst and the EIE (enzyme interesterification) process using Novozymes Lipozyme® TL IM immobilized enzyme. In the CIE process, 400-500 g of the dried oil blend was heated to 95-105° Celsius, and 0.1-0.2% sodium methoxide catalyst was added and allowed to react for 40-60 minutes in a glass stirred reactor. In the EIE process, a laboratory scale enzyme treatment system was configured as three columns in series, each column being 250 millimeters in height, with an internal diameter 10 millimeters, and containing roughly 7 grams of Novozymes Lipozyme® XL IM enzyme, each of the columns being packed in a configuration generally indicated as column type "1" in FIG. 5. In the top and bottom of each column, a small amount of glass beads (2 mm diameter) is retained between layers of glass wool and positioned in the column to retain the immobilized enzyme in the column and not plug the connections between the columns. A 5.2 kg sample of the oil blend was heated to 70° Celsius at which it was in the liquid state, and pumped at a constant flow rate of about 2 grams of oil per gram of enzyme per hour through the treatment system. This process produced 3.8 kg of enzymatically interesterified oil, which corresponds to a productivity or full conversion of 0.14 kg of oil per gram of enzyme (3.8 kg/21 g of enzyme).

It was found that the melt profiles of the products produced by the CIE and EIE processes were essentially identical. Table I below sets forth the solid fat content (SFC) of each of the CIE and EIE products at various temperatures of interest, and compares them to the specification for the desired zero trans fat margarine product. The tocopherol level in the CIE oil was 50% of the tocopherol level in the EIE oil. It may be seen that the EIE process preserved almost all of the beneficial tocopherol originally present in the oil blend prior to any interesterification, while the CIE process destroyed about 50% of the tocopherol.

TABLE 1

|  | Fully Hydrog Base (60% PKO/40% PO) | Chemically Interesterified Base | Enzymatically Interesterified Base | Specification |
|---|---|---|---|---|
| SFC 10.0° C. | 95.6 | 96.7 | 97.2 | min. 95.5 |
| 21.1° C. | 89.2 | 91.4 | 94.6 | 86.0-95.0 |
| 26.7° C. | 79.3 | 79.9 | 84.9* | 75.0-84.0 |
| 33.3° C. | 58.5 | 53.0 | 59.1* | 50.0-58.0 |
| 37.8° C. | 51.4 | 27.8* | 34.0 | 28.0-36.0 |
| 40.0° C. | 47.8 | 16.4* | 22.8 | 18.5-26.0 |
| 45.0° C. | 37.7 | 1.7* | 5.9 | 2.5-7.0 |
| 50.0° C. | 20.7 | 0.0 | 0.1 | — |
| Dropping Point (° C.) | 54.6 | 45.8* | 47.6 | 48.0-51.0 |
| Tocopherols (ppm) | 147 | 75 | 146 | — |

To further evaluate the products of the CIE and EIE processes, the products were blended into oil compositions with 14.0% of the interesterification product, 85.5% soybean oil, and 1.5% fully hydrogenated palm oil. Table 2 below sets forth the solid fat content of the two blends at various temperatures of interest. The stability of the oil compositions, as measured by a Rancimat Metrohm (model 743) at 130° Celsius, was 10 hours for the blend utilizing the CIE product and 20 hours for the blend utilizing the EIE product.

TABLE 2

| | 14.0% Chemical Interesterified Base 85.5% Soybean Oil 1.5% FH Palm Oil | 14.0% Enzymatic Interesterified Base 85.5% Soybean Oil 1.5% FH Palm Oil | Specification |
|---|---|---|---|
| SFC 10.0° C. | 14.7 | 13.4 | 14.5-16.5 |
| 21.1° C. | 8.1 | 7.6 | 8.0-10.0 |
| 26.7° C. | 5.3 | 5.0 | 5.0-7.0 |
| 33.3° C. | 2.6 | 2.4 | 2.5-3.5 |
| 37.8° C. | 0.9 | 1.0 | 1.0-2.0 |
| 40.0° C. | 0.2 | 0.0 | 0.3-0.8 |
| Dropping Point (° C.) | 36.3 | 36.0 | 35.0-38.0 |
| Rancimat (hours) | 10 | 20 | |

Example 2

Evaluation of Citric Acid as Pre-Treatment Process Aid

Comparative Example

Figure 5:
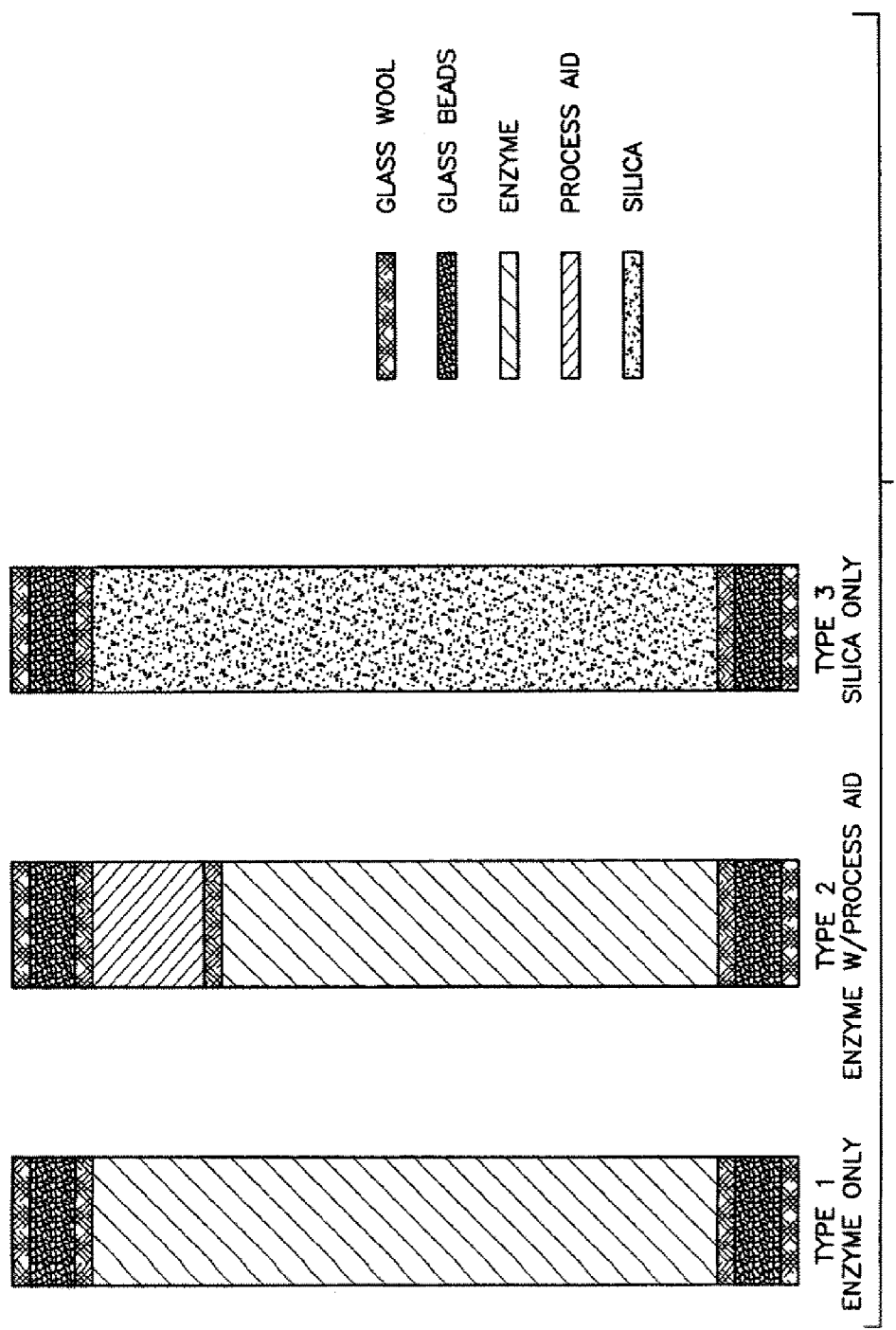
FIG. 5 illustrates three different types of packed columns suitable for use in various embodiments of the present invention.

It has been suggested that trace metals present in oil products can oxidize the oil and cause premature de-activation of the enzyme. Citric acid will act as a chelation agent for trace metals, resulting in their inactivation, as reported by Dutton et al. in the J.A.O.C.S. (1948 and 1949). Accordingly, citric acid was tested as a pre-treatment process aid to determine if it would result in prolonged enzymatic activity in a subsequent EIE process. Two trials of citric acid as a pre-treatment process aid were conducted. A laboratory scale enzyme interesterification treatment system as described in Example 1 was used, but using three columns connected in series. The second and third columns in the series were of Type "1" as illustrated in FIG. 5 and used in Example 1 above, but the first column was of Type "2" illustrated in FIG. 5. Each of the three columns was packed with roughly 7 grams of Novozymes Lipozyme® TL IM enzyme, along with glass wool and glass beads on top and bottom of the enzymes in each column as described in Example 1. In the first column of Type 2, 0.80 grams of granular citric acid (obtained from Tate and Lyle, product code 510 104 176) was added (1 cm height) on top of the bed of enzymes as a process aid. In the first trial, a total of 21.57 grams of enzyme was used. In each trial, a 5.2 kg sample of the oil blend as described above was brought to 70° Celsius and allowed to run through the three columns for a period of about five days at a flow rate of about 2.0 g of fat/g of enzyme/h.

Table 3 below lists the properties of the oil used in this example after bleaching but before being subjected to enzyme interesterification. It may be seen that all but two of the properties were within range of the an internal specifications for this product type.

American Oil Chemists' Society Official Methods

| Free Fatty Acid (FFA) | Ca 5a-40 |
| Trace Metals (P, Fe, Cu, and Ni) | Ca 18b-91 |
| Anisidine Index | Cd 18-90 |
| Peroxide Value (PV) | Ca 8b-90 |
| Dropping Point | Cc 18-80 |
| Moisture | Ca 2e-84 |
| Solid Fat Content | Cd 16b-93 |
| Tocopherols | Ce 8-89 |
| Rancimat | Cd 12b-92 |

TABLE 3

| ANALYSES | BEFORE EIE (after bleaching treatment) | SPECIFICATION |
|---|---|---|
| FFA (% as oleic) | 0.105 | Max. 0.15 |
| Phosphorous (ppm) | 0.87 | Max. 5.0 |
| Anisidine Index | 0.81 | Max. 2.0 |
| Iron (ppm) | <0.5 | Max. 0.5 |
| Copper (ppm) | — | Max. 0.5 |
| Nickel (ppm) | — | Max. 0.5 |
| Peroxide Value (meq/Kg) | 0.0 | Max. 2.0 |
| Dropping Point (° C.) | 55.0 | 54.0-56.0 |
| Soap (ppm) | 0.0 | Max. 5.0 |
| Solids - SFC (%) 10.0° C. | 93.4 | 93.0-96.0 |
| 21.1° C. | 86.3* | 87.0-91.0 |
| 26.7° C. | 75.4* | 76.0-80.0 |
| 33.3° C. | 56.3 | 55.0-59.0 |
| 37.8° C. | 48.9 | 48.0-52.0 |
| 40.0° C. | 45.3 | 44.0-48.0 |
| 45.0° C. | 35.1 | 34.0-38.0 |
| 50.0° C. | 18.0 | 18.0-20.0 |
| Moisture (%) | 0.003 | 0.01 |

Table 4 below lists the properties of the oil product after EIE treatment in the three columns with the citric acid pre-treatment in the first trial. It may be seen that as the test continued to the fifth day, more of the properties did not meet the specification for the product, particularly the solid fats content at elevated temperatures.

TABLE 4

| AFTER EIE | Day 1 | Day 2 | Day 3 | Day 4 | Day 5 | Spec |
|---|---|---|---|---|---|---|
| Flow rate (g/hr) | 59.97 | 61.0 | 56.73 | 57.49 | 61.65 | |
| FFA (% as oleic) | 0.554 | 0.564 | 0.737 | 0.672 | 0.745 | — |
| Peroxide Value (meq/Kg) | 0.91 | 0.29 | 0.84 | 0.70 | 0.49 | — |
| Dropping Point (° C.) | 46.7 | 47.7 | 48.5 | 51.3* | 52.3* | 46.0-49.0 |
| Solids - SFC (%) 10.0° C. | 96.7 | 96.9 | 96.6 | 95.3* | 95.0 | Min 95.0 |
| 21.1° C. | 91.9 | 92.1 | 91.4 | 89.5 | 88.9 | 88.0-94.0 |
| 26.7° C. | 79.9 | 80.1 | 79.5 | 78.0 | 77.1 | 76.0-84.0 |
| 33.3° C. | 53.7 | 54.1 | 54.0 | 53.9 | 53.6 | 52.0-58.0 |
| 37.8° C. | 30.3 | 31.4 | 34.1 | 39.6* | 41.5* | 29.0-36.0 |
| 40.0° C. | 21.0 | 22.9 | 26.6* | 34.2* | 36.5* | 20.0-26.0 |
| 45.0° C. | 5.1 | 7.2 | 11.4* | 20.8* | 24.0* | 4.0-7.0 |

After 2 days of production, the product deviated outside the SFC product specification, indicating that the reaction was no longer going to completion while the constant flow rate was maintained. To achieve more complete reaction, it would have been necessary to slow the flow rate of the composition through the system, contrary to a purpose of the present invention. Over a five day period (only the first two of which resulted in acceptable product), the process yielded 2.4 kg of interesterified fat that met the desired product specifications, corresponding to a productivity or conversion of 0.11 kg of fat per gram of enzyme (2.4 kg/21.57 g of enzyme).

In the second trial, oil from the same source was passed through the same arrangement of columns containing 0.80 grams of citric acid and 20.79 grams of enzyme, at the same flow rate and temperature as the first trial, but for a period of only four days. The properties of the oil after bleaching but before EIE treatment are set forth in Table 5 below. This sample of the starting oil was pulled from the same original blend, however, it had a slightly different analysis from the sample used in the first trial.

TABLE 5

| ANALYSES | BEFORE EIE (after bleaching treatment) | SPECIFICATION |
|---|---|---|
| FFA (% as oleic) | 0.148 | Max. 0.15 |
| Phosphorous (ppm) | 1.21 | Max. 5.0 |
| Anisidine Index | 0.55 | Max. 2.0 |
| Iron (ppm) | <0.5 | Max. 0.5 |
| Peroxide Value (meq/Kg) | 0.07 | Max. 2.0 |
| Dropping Point (° C.) | 56.7* | 54.0-56.0 |
| Soap (ppm) | 0.0 | Max. 5.0 |
| Solids - SFC (%) 10.0° C. | 94.7 | 93.0-96.0 |
| 21.1° C. | 87.8 | 87.0-91.0 |
| 26.7° C. | 77.7 | 76.0-80.0 |
| 33.3° C. | 58.3 | 55.0-59.0 |
| 37.8° C. | 50.9 | 48.0-52.0 |
| 40.0° C. | 47.5 | 44.0-48.0 |
| 45.0° C. | 37.2 | 34.0-38.0 |
| 50.0° C. | 20.4* | 18.0-20.0 |
| Moisture (%) | 0.005 | 0.01 |

Table 6 below sets forth the properties of the oil after 4 days of treatment through the EIE system. After four days, the value for the solid fats content at 45.0° Celsius deviated significantly from the specification, and the evaluation was discontinued.

TABLE 6

| AFTER EIE | Day 1 | Day 4 | SPEC |
|---|---|---|---|
| Flow rate (g/hr) | 65.95 | 32.8 | — |
| FFA (% as oleic) | 0.408 | 0.450 | — |
| Peroxide Value (meq/Kg) | 0.31 | 0.11 | — |
| Anisidine Index | 0.89 | 0.84 | — |
| Dropping Point (° C.) | 47.2 | 48.3 | 46.0-49.0 |
| Solids - SFC (%) 10.0° C. | 97.1 | 97.3 | Min 95.0 |
| 21.1° C. | 93.6 | 94.0 | 88.0-94.0 |
| 26.7° C. | 83.2 | 83.0 | 76.0-84.0 |
| 33.3° C. | 57.9 | 57.9 | 52.0-58.0 |
| 37.8° C. | 33.8 | 34.6 | 29.0-36.0 |
| 40.0° C. | 23.6 | 24.6 | 20.0-26.0 |
| 45.0° C. | 6.2 | 7.9* | 4.0-7.0 |

After four days, this trial yielded 3.5 kg of interesterified fat, corresponding to a productivity of 0.17 kg fat/g enzyme. The reason for the difference in productivity between the two trials was not determined, but it is theorized that the solubility of citric acid in the oil had some affect. Both trials with citric acid demonstrated a very low conversion/productivity. Comparison of the SFC content at 40° C. between the no pretreatment trial of Example 1 and the citric acid pretreatment of this Example 2 leads to the conclusion that citric acid does not increase the life of the enzyme, but actually acts a poison.

Example 3
Evaluation of EDTA as Pre-Treatment Process Aid

Comparative Example

As it was concluded that the two trials from Example 2 that citric acid exhibited a "poisoning" effect on the enzyme, it was thought that a different chelation agent might have a positive affect on the enzyme's activity by removing the trace metals present in the oils. EDTA (Disodium Ethylenediamine Tetraacetic Acid) is known as a chelation agent for the inactivation of trace metals.

Two trials of EDTA as a pre-treatment process aid were conducted. A type "2" column and two type "1" columns were arranged in series as described in Example 2 above. The three columns arranged contained a total of 21.3 g of the same enzyme as described above. For the first trial, 0.43 grams of micro-granular EDTA (obtained from Aksell Quimica (Indaiatuba, SP Brazil) product code 1282710200) was used as the process aid on top of the bed of enzymes in the first column, 1 cm height. A sample of the same oil blend as was used in Examples 1 and 2 was run through the columns over a period of seven days at a flow rate of 2.0 g of fat/g of enzyme/hour at a temperature of 70° Celsius. Table 7 below sets forth the properties of the oil before enzyme treatment. Table 8 sets forth the properties of the oil after the enzyme treatment with EDTA pre-treatment.

TABLE 7

| ANALYSES | BEFORE EIE (after bleaching treatment) | SPECIFICATION |
|---|---|---|
| FFA (% as oleic) | 0.241* | Max. 0.15 |
| Phosphorous (ppm) | 1.21 | Max. 5.0 |
| Anisidine Index | 0.95 | Max. 2.0 |
| Iron (ppm) | <0.5 | Max. 0.5 |
| Copper (ppm) | — | Max. 0.5 |
| Nickel (ppm) | — | Max. 0.5 |
| Peroxide Value (meq/Kg) | 0.0 | Max. 2.0 |
| Dropping Point (° C.) | 56.7* | 54.0-56.0 |
| Soap (ppm) | 0.0 | Max. 5.0 |
| Solids - SFC (%) 10.0° C. | 94.7 | 93.0-96.0 |
| 21.1° C. | 87.8 | 87.0-91.0 |
| 26.7° C. | 77.7 | 76.0-80.0 |
| 33.3° C. | 58.3 | 55.0-59.0 |
| 37.8° C. | 50.9 | 48.0-52.0 |
| 40.0° C. | 47.5 | 44.0-48.0 |
| 45.0° C. | 37.2 | 34.0-38.0 |
| 50.0° C. | 20.4* | 18.0-20.0 |
| Moisture (%) | — | 0.01 |

TABLE 8

| AFTER EIE | Day 1 | Day 4 | Day 6 | SPEC |
|---|---|---|---|---|
| Flow rate (g/hr) | 53.17 | 49.3 | 55.7 | — |
| FFA (% as oleic) | — | — | 0.580 | — |
| Peroxide Value (meq/Kg) | — | — | 0.44 | — |
| Anisidine Index | — | — | 1.08 | — |
| Dropping Point (° C.) | — | 47.5 | 47.8 | 46.0-49.0 |
| Solids - SFC (%) 10.0° C. | — | 97.2 | 97.2 | Min 95.0 |
| 21.1° C. | — | 93.8 | 93.9 | 88.0-94.0 |
| 26.7° C. | — | 82.6 | 83.0 | 76.0-84.0 |
| 33.3° C. | — | 57.7 | 57.5 | 52.0-58.0 |
| 37.8° C. | — | 34.2 | 34.2 | 29.0-36.0 |
| 40.0° C. | — | 23.5 | 24.9 | 20.0-26.0 |
| 45.0° C. | — | 5.6 | 7.5* | 4.0-7.0 |

The trial was stopped after six days due to high pump pressure. Apparently the EDTA processing aid had become compacted in the bed. This trial yielded 7.2 kg of interesterified fat corresponding to a productivity or conversion of 0.39 kg of fat per g of enzyme.

For the second trial, the set-up was identical to the first trial, with a total of 21.3 g of enzyme in three columns connected in series and a flow rate of 2.0 g of fat/g of enzyme/h, except that a mixture of EDTA (0.43 grams) and glass beads (2 mm in diameter) in a ratio of 75:25 was used as the processing aid in an attempt to improve the flow rate and reduce the pressure of pumping. The EDTA/glass bead mixture was placed on top of the enzyme in the first column to a height of 1 cm. The properties of the oil prior to treatment are set forth in Table 9, and the properties of the oil after treatment are set forth in Table 10.

TABLE 9

| ANALYSES | BEFORE EIE (after bleaching treatment) | SPECIFICATION |
| --- | --- | --- |
| FFA (% as oleic) | 0.096 | Max. 0.15 |
| Phosphorous (ppm) | 1.09 | Max. 5.0 |
| Anisidine Index | 1.14 | Max. 2.0 |
| Iron (ppm) | <0.1 | Max. 0.5 |
| Copper (ppm) | — | Max. 0.5 |
| Nickel (ppm) | — | Max. 0.5 |
| Peroxide Value (meq/Kg) | 0.0 | Max. 2.0 |
| Dropping Point (° C.) | 54.8 | 54.0-56.0 |
| Soap (ppm) | 1.4 | Max. 5.0 |
| Solids - SFC (%) 10.0° C. | 94.6 | 93.0-96.0 |
| 21.1° C. | 87.8 | 87.0-91.0 |
| 26.7° C. | 77.3 | 76.0-80.0 |
| 33.3° C. | 57.3 | 55.0-59.0 |
| 37.8° C. | 50.0 | 48.0-52.0 |
| 40.0° C. | 46.6 | 44.0-48.0 |
| 45.0° C. | 36.3 | 34.0-38.0 |
| 50.0° C. | 19.9 | 18.0-20.0 |
| Moisture (%) | — | 0.01 |

TABLE 10

| AFTER EIE | Day 1 | Day 3 | Day 6 | Day 8 | Day 9 Cancelled | SPEC |
| --- | --- | --- | --- | --- | --- | --- |
| Flow rate (g/hr) | 42.44 | 41.6 | 50.96 | 72.5 | — | — |
| FFA (% as oleic) | 0.894 | 0.940 | 0.944 | 0.815 | — | — |
| Peroxide Value (meq/Kg) | 0.0 | 0.08 | 0.13 | 0.12 | — | — |
| Anisidine Index | 1.19 | — | — | 1.21 | — | — |
| Dropping Point (° C.) | 46.4 | 46.5 | 46.9 | 47.4 | — | 46.0-49.0 |
| Solids - SFC (%)10.0° C. | 97.0 | 97.0 | 97.1 | 97.0 | — | Min 95.0 |
| 21.1° C. | 92.4 | 92.6 | 93.0 | 93.3 | — | 88.0-94.0 |
| 26.7° C. | 80.6 | 80.9 | 81.4 | 82.1 | — | 76.0-84.0 |
| 33.3° C. | 54.4 | 54.7 | 55.3 | 56.5 | — | 52.0-58.0 |
| 37.8° C. | 31.2 | 31.2 | 31.5 | 33.4 | — | 29.0-36.0 |
| 40.0° C. | 20.8 | 20.9 | 21.7 | 23.9 | — | 20.0-26.0 |
| 45.0° C. | 3.8* | 4.2 | 5.2 | 7.3* | — | 4.0-7.0 |

This second trial, like the first trial, showed a compaction of the EDTA. The glass beads used in the second trial slowed the rate of compaction, but after eight days the trial had to be terminated due to high pump pressure. This second trial yielded 9.6 kg of interesterified fat corresponding to a productivity or conversion of 0.45 kg of fat per g of enzyme. The EDTA improved the system productivity by roughly 100 percent over the EIE system of Example 1 above in which no processing aid was used.

Example 4

Evaluation of Silica Gel as Pre-Treatment Process Aid

Four columns were prepared and arranged in series for this test. The first column in the series was configured as type "3" as illustrated in FIG. 5, using a bed of chromatographic grade silica available under the designation SP 535-10065 (3.3 g of silica) from W. R. Grace; this silica gel is substantially moisture free with approximately 316 m$^2$/g of surface area, pore volume of 1.029 ml/g, a pH of 6.8, total volatiles of 4.4 percent, tamped density of 358 g/l, an average pore density of 163 angstroms, particle size distribution between 100 and 300 microns, a mesh size of 50 to 150, and SiO$_2$ content of 99.7% on a dry basis. The other three columns in the series were configured as type columns as illustrated in FIG. 5, packed in with a total of 22.0 g of Novozymes Lipozyme® TL IM, the same immobilized enzyme product that was used in each of the previous three examples. The ratio of silica to enzyme was about 15%. The trial was run with the same oil blend as used in the previous three examples. The trial continued for thirty three days at a flow rate of 2.0 g of fat/g of enzyme/h.

Table 11 below sets forth the properties of the oil prior to enzyme treatment, and Tables 12 and 13 set forth the properties of the oil after the enzyme treatment with silica pre-treatment, the silica being substantially moisture free. The activity and stability of the enzymatic process may be measured by the changes in the 45 and 40° Celsius SFC readings.

TABLE 11

| ANALYSES | BEFORE EIE (after bleaching treatment) | SPECIFICATION |
| --- | --- | --- |
| FFA (% as oleic) | 0.072 | Max. 0.15 |
| Phosphorous (ppm) | 1.05 | Max. 5.0 |
| Anisidine Index | 1.06 | Max. 2.0 |
| Iron (ppm) | <0.1 | Max. 0.5 |
| Copper (ppm) | <0.02 | Max. 0.5 |
| Nickel (ppm) | <0.5 | Max. 0.5 |
| Peroxide Value (meq/Kg) | 0.0 | Max. 2.0 |

TABLE 11-continued

| ANALYSES | BEFORE EIE (after bleaching treatment) | SPECIFICATION |
| --- | --- | --- |
| Dropping Point (° C.) | 54.4 | 54.0-56.0 |
| Soap (ppm) | 4.7 | Max. 5.0 |
| Solids - SFC (%) 10.0° C. | 92.5* | 93.0-96.0 |
| 21.1° C. | 85.2* | 87.0-91.0 |
| 26.7° C. | 74.5* | 76.0-80.0 |
| 33.3° C. | 55.8 | 55.0-59.0 |
| 37.8° C. | 48.8 | 48.0-52.0 |
| 40.0° C. | 45.4 | 44.0-48.0 |
| 45.0° C. | 35.3 | 34.0-38.0 |
| 50.0° C. | 19.2 | 18.0-20.0 |
| Moisture (%) | 0.007 | 0.01 |

TABLE 12

| AFTER EIE | Day 3 | Day 6 | Day 8 | Day 10 | Day 13 | Day 15 | Day 17 | Day 20 | SPEC |
|---|---|---|---|---|---|---|---|---|---|
| Flow rate (g/hr) | 47.5 | 46.8 | 44.7 | 44 | 44 | 45 | 46 | — | |
| FFA (% as oleic) | — | 0.481 | — | — | 0.506 | — | — | 0.476 | — |
| PV (meq/Kg) | — | 0.72 | — | — | 0.60 | — | — | 0.34 | — |
| Anisidine Index | — | 1.62 | — | — | 0.35 | — | — | — | — |
| Dropping Point (° C.) | 46.4 | 46.5 | 46.7 | 46.8 | 47.0 | 47.1 | 47.3 | 47.5 | 46.0-49.0 |
| Solids-SFC (%)10.0° C. | 96.9 | 96.4 | 96.7 | 97.0 | 97.0 | 97.0 | 97.0 | 97.0 | Min 95.0 |
| 21.1° C. | 91.1 | 91.2 | 92.7 | 91.8 | 91.8 | 91.8 | 91.5 | 92.2 | 88.0-94.0 |
| 26.7° C. | 78.6 | 78.7 | 80.2 | 79.5 | 79.3 | 79.4 | 79.2 | 79.9 | 76.0-84.0 |
| 33.3° C. | 52.2 | 52.5 | 54.1 | 53.4 | 52.8 | 52.8 | 52.7 | 53.8 | 52.0-58.0 |
| 37.8° C. | 29.1 | 29.4 | 30.8 | 30.2 | 29.9 | 30.5 | 30.2 | 31.0 | 29.0-36.0 |
| 40.0° C. | 19.0* | 19.3* | 21.0 | 20.5 | 20.8 | 21.2 | 21.5 | 22.0 | 20.0-26.0 |
| 45.0° C. | 3.7* | 4.0 | 5.1 | 4.8 | 5.3 | 5.8 | 5.7 | 6.2 | 4.0-7.0 |

TABLE 13

| AFTER EIE | Day 22 | Day 23 | Day 27 | Day 28 | Day 29 | Day 31 | Day 33 | Day 36 | SPEC |
|---|---|---|---|---|---|---|---|---|---|
| Flow rate (g/hr) | 44.6 | 44.6 | 42.9 | 41.1 | 48.3 | 44.6 | 39.8 | 42.7 | |
| FFA (% as oleic) | — | — | — | 0.530 | — | — | — | — | — |
| PV (meq/Kg) | — | — | — | 0.39 | — | — | — | — | — |
| Anisidine Index | — | — | — | 2.10 | — | — | — | — | — |
| Dropping Point (° C.) | 47.6 | 47.8 | 48.4 | 48.4 | 48.7 | 48.8 | 48.8 | 50.5 | 46.0-49.0 |
| Solids-SFC (%) 10.0° C. | 97.0 | 96.7 | 97.1 | 97.0 | 96.3 | 97.0 | 96.8 | 96.6 | Min 95.0 |
| 21.1° C. | 92.9 | 92.6 | 92.9 | 92.8 | 91.8 | 92.4 | 92.2 | 91.8 | 88.0-94.0 |
| 26.7° C. | 81.3 | 81.6 | 81.4 | 81.3 | 81.3 | 81.1 | 80.4 | 80.6 | 76.0-84.0 |
| 33.3° C. | 55.5 | 56.0 | 55.6 | 55.3 | 55.6 | 55.1 | 55.2 | 55.5 | 52.0-58.0 |
| 37.8° C. | 32.7 | 33.3 | 33.9 | 34.5 | 34.6 | 34.5 | 34.6 | 36.0 | 29.0-36.0 |
| 40.0° C. | 23.6 | 24.2 | 25.0 | 24.8 | 26.5* | 26.4* | 26.9* | 28.4* | 20.0-26.0 |
| 45.0° C. | 7.9* | 8.3* | 9.2* | 9.3* | 11.1* | 10.9* | 11.6* | 13.4* | 4.0-7.0 |

The process produced 40 kg of an interesterified fat that met the internal specification with a stable system. The productivity of the enzyme was calculated at 1.82 kg of fat per gram of enzyme, representing a greater than 1000% increase in activity over the enzyme activity without any pretreatment, based on the productivity of 0.14 kg oil/g enzyme. An analysis of the oil before and after the silica pre-treatment but before enzyme treatment showed no substantial difference in commonly measured industry criteria. Without wishing to be bound by theory, it is believed that the substantially moisture-free silica is removing an as yet uncharacterized substance in the lipid-containing composition.

TABLE 14

| ANALYSIS | BEFORE SILICA | AFTER SILICA |
|---|---|---|
| FFA (% oleic acid) | 0.443 | 0.440 |
| Soap (ppm) | 10.30 | 9.06 |
| Metals Cu | <0.02 | <0.02 |
| Fe | <0.1 | <0.1 |
| Ni | <0.5 | <0.5 |
| Phosphorus (ppm) | 0.413 | 0.318 |
| Anisidine Value | 1.19 | 1.16 |
| Peroxide Value (meq/Kg) | 0.588 | 0.600 |

FIG. 6 is a graph illustrating solid fat content data from the trials of Example 1 with no pre-treatment, Example 2 with citric acid pre-treatment, and Example 4 with substantially moisture-free silica pre-treatment. It may be seen that pre-treatment with citric acid provides a negative effect, i.e., the result is even worse than that obtained with no pre-treatment at all. The line of data from pre-treatment with a substantially moisture free silica shows a significantly lower slope, and is capable of running over a much longer test period.

The foregoing results demonstrate that citric acid is detrimental to the activity of the enzyme and the overall conversion of the material to be interesterified. EDTA in the powder form tested is not acceptable due to the compression of the bed and pressure build-up, even when mixed with glass beads to improve process flow. Substantially moisture free silica was found to be extremely beneficial for the activity and life of the enzyme catalyst. Moreover, these results were achieved with far less silica than has been disclosed in other prior art laboratory scale processes. The process of Example 4 herein used 3.3 g substantially moisture free silica per 22.0 g immobilized enzyme, or about 15%. In U.S. Pat. Appl. Publ. No. 2003/0054509 and U.S. Pat. Appl. Publ. No. 2005/0014237, in Examples 3, it is reported that 38 grams of a silica product that is presumably not moisture free are used per 22 grams of enzyme, or about 172%. Thus the present invention allows a drastic reduction in the amount of pre-treatment medium while still obtaining a high quality interesterified product in a continuous process.

Example 5

Industrial Process

Control

The industrial Enzymatic Interesterification (EIE) scale process was configured according to FIG. 4 except that only four columns were placed in series and packed with 20 kg of Novozymes Lipozyme® TL IM each for a total of 80 kg of enzyme. The same immobilized enzyme product that was used in each of the previous four examples was utilized in this example. The industrial process is operated in a continuous mode where four reactors are placed in series according to FIG. 4. The reactors are designated as "A", "B", "C", and "D" in the industrial plant from left to right. A reactor sequence of "CDBA" means that reactor "C" is the first reactor to come into contact with the lipid material followed by reactors "D", "B", and "A". Reactor "C" would be the reactor that has been online the longest, while reactor "A" would be packed with new enzyme. The reactor configuration during this trial was "ABCD". Prior to the trial of this Example 5, the reactors had processed 10 tons of a deodorized base oil to meet product specifications. In this control example, the industrial configuration was not equipped with a pretreatment system, nor was a process aid used in any of the columns. A quantity of the same oil as used in Examples 1-4 above was held in a tank at liquid temperature (generally 70-100° C.), and was pumped at a constant flow rate of 200 kg/hr through a heat exchanger to cool the oil to 70° C., and then through the series of packed columns to contact the enzyme.

Table 15 below sets forth the properties of the oil prior to enzyme treatment and Table 16 sets forth the properties of the oil after the enzyme treatment without any pretreatment.

TABLE 15

| ANALYSES | BEFORE EIE (after bleaching treatment) | SPECIFICATION |
|---|---|---|
| FFA (% as oleic) | 0.17 | Max. 0.15 |
| Phosphorous (ppm) | 1.05 | Max. 5.0 |
| Anisidine Index | — | Max. 2.0 |
| Iron (ppm) | — | Max. 0.2 |
| Copper (ppm) | — | Max. 0.05 |
| Nickel (ppm) | below detection | Max. 0.2 |
| Peroxide Value (meq/Kg) | 0.0 | Max. 1.0 |
| Dropping Point (° C.) | 55.1* | 53.0-55.0 |
| Soap (ppm) | 0.0 | Max. 5.0 |
| Solids - SFC (%) 10.0° C. | 94.9 | 94.0-96.0 |
| 20.0° C. | — | 89.0-91.0 |
| 30.0° C. | — | 65.0-67.0 |
| 35.0° C. | — | 52.0-54.0 |
| 40.0° C. | 46.4* | 44.0-46.0 |
| 50.0° C. | 35.1* | 32.0-34.0 |
| 55.0° C. | 18.9 | 18.0-20.0 |
| 50.0° C. | 0.0 | 0.0 |
| Moisture (%) | 0.007 | Max. 0.02 |

TABLE 16

| AFTER EIE | Day 1 | Day 2 | Day 2 | Day 3 | Day 4 | SPEC. |
|---|---|---|---|---|---|---|
| Flow rate (kg/hr) | 200 | 200 | 170 | 170 | 170 | — |
| FFA (% as oleic) | 0.98 | — | 0.67 | 0.52 | 0.75 | — |
| Dropping Point (° C.) | 48.7* | 48.2* | 49.2* | 51.6* | 47.8* | 45.0-47.0 |
| Solids-SFC (%) 10.0° C. | 96.1 | 96.6 | 96.5 | 96.5 | 96.3 | 96.0-98.0 |
| 21.1° C. | 88.7* | 92.4 | 92.5 | 92.4 | 90.1 | 91.0-93.0 |
| 26.7° C. | 76.2* | 79.4* | 80.5 | 80.0 | 76.8* | 80.0-82.0 |
| 33.3° C. | 52.0* | 53.8* | 55.9 | 55.4 | 51.1* | 54.0-56.0 |
| 37.8° C. | 31.1* | 34.0 | 37.2* | 38.9* | 31.5* | 32.0-34.0 |
| 40.0° C. | 24.8* | 26.0* | 27.9* | 33.4* | 23.7 | 22.0-24.0 |
| 45.0° C. | 8.2* | 9.5* | 12.7* | 16.6* | 7.5* | 4.0-6.0 |

20 metric tonnes of blended oil were processed during the four day process trial. The oil flow was reduced on day two in an attempt to produce material that would meet the product specification. The process was stopped after four days because the product did not meet the required specifications. The productivity or conversion for this trial period is zero (kg/g), because no oil produced met the product specifications.

Example 6

Industrial Process with Silica Pretreatment

The industrial process with silica was configured the same as Example 5, except when each of the reactors required new enzyme, they were packed with 20 kg of Novozymes Lipozyme® TL IM followed by 3 kg of substantially moisture free chromatographic silica (SP 535-10065 sold by W. R. Grace), i.e., each column was packed as a type "2" column in FIG. 5, with the substantially moisture-free silica used as the process aid. The process continued to run until each column had been re-packed to be a type "2" column, then the evaluation for this Example commenced. Batches of the same oil blend used in Examples 1-5 above were pumped through the system at a constant flow rate of 200 kg/hr the first day and 170 kg/hr for each day thereafter, at a temperature of 70° C., the oil contacting first the silica and then the enzyme in each of the columns. Table 17 below sets forth the characteristics of the oil blends used in this Example as sampled on the first, sixty-ninth, and one hundred first days of the evaluation prior to EIE treatment, and Table 18 below sets forth the characteristics of the interesterified oil as sampled on those same days of the evaluation.

TABLE 17

| ANALYSES | BEFORE EIE Day 1 | BEFORE EIE Day 69 | BEFORE EIE Day 101 | SPECIFICATION |
|---|---|---|---|---|
| FFA (% as oleic) | 0.09 | 0.112 | 0.15 | Max. 0.15 |
| Phosphorous (ppm) | 1.1 | 1.2 | 1.2 | Max. 5.0 |
| Anisidine Index | 0.0 | 0.0 | 0.0 | Max. 2.0 |
| Iron (ppm) | <0.1 | <0.1 | <0.1 | Max. 0.5 |
| Copper (ppm) | <0.02 | <0.02 | <0.02 | Max. 0.5 |
| Nickel (ppm) | <0.5 | <0.5 | <0.5 | Max. 0.5 |
| Peroxide Value (meq/Kg) | 0.0 | 0.0 | 0.0 | Max. 2.0 |
| Dropping Point (° C.) | 55.1 | 54.7 | 56.3 | 54.0-56.0 |
| Soap (ppm) | 0.0 | 0.0 | 0.0 | Max. 5.0 |
| Solids - SFC (%) 10.0° C. | 95.5 | 95.5 | 95.3 | 93.0-96.0 |
| 21.1° C. | 90.7 | 90.1 | 89.8 | 87.0-91.0 |
| 26.7° C. | 78.2 | 78.3 | 77.6 | 76.0-80.0 |
| 33.3° C. | 57.2 | 56.3 | 56.4 | 55.0-59.0 |

TABLE 17-continued

| ANALYSES | BEFORE EIE Day 1 | BEFORE EIE Day 69 | BEFORE EIE Day 101 | SPECIFICATION |
|---|---|---|---|---|
| 37.8° C. | 49.5 | 48.9 | 48.6 | 48.0-52.0 |
| 40.0° C. | 45.8 | 45.3 | 45.2 | 44.0-48.0 |
| 45.0° C. | 37.7 | 35.1 | 35.1 | 34.0-38.0 |
| 50.0° C. | 20.3 | 19.5 | 18.1 | 18.0-20.0 |
| Moisture (%) | 0.0 | 0.0 | 0.0 | 0.01 |

TABLE 18

| AFTER EIE | Day 1 | Day 69 | Day 101 | Specification |
|---|---|---|---|---|
| Flowrate (kg/h) | 200 | 174 | 172 | |
| FFA (% as oleic) | 0.70 | 0.46 | 0.62 | |
| Peroxide Value (meq/Kg) | 0.0 | 0.0 | 0.0 | |
| Dropping Point (° C.) | 48.7 | 47.5 | 48.8 | 46.0-49.0 |
| Solids - SFC (%) 10.0° C. | 96.7 | 96.8 | 96.7 | Min. 95.0 |
| 21.1° C. | 93.6 | 93.9 | 93.6 | 88.0-94.0 |
| 26.7° C. | 83.2 | 83.6 | 82.7 | 76.0-84.0 |
| 33.3° C. | 59.5 | 56.7 | 57.6 | 52.0-58.0 |
| 37.8° C. | 33.2 | 32.6 | 32.2 | 29.0-36.0 |
| 40.0° C. | 23.1 | 22.3 | 22.3 | 20.0-26.0 |
| 45.0° C. | 8.5* | 6.3 | 5.8 | 4.0-7.0 |

In order to determine the productivity of the enzyme being utilized in a continuous system, a "cycle" for each column was defined. A cycle consists of a new reactor being placed online as the fourth, then the third, second, and finally the first reactor in the series. Cycle 1 below in Table 19 is the cycle for reactor "A", i.e. for reactor A cycle 1 goes from Day 1 to Day 69. Each time the reactor sequence was changed as shown in Table 19, the procedure was followed as described above in relation to FIG. 4, and the rate of flow through the system remained constant.

TABLE 19

| Start Date | Finish Date | Reactor Sequence | Product Produced (kg) | Cycle 1 | 2 | 3 | 4 |
|---|---|---|---|---|---|---|---|
| Day 1 | Day 6 | BCDA | 28,000 | | | | |
| Day 6 | Day 28 | CDAB | 86,000 | | | | |
| Day 28 | Day 33 | DABC | 20,000 | | | | |
| Day 33 | Day 69 | ABCD | 56,000 | | | | |
| Day 69 | Day 76 | BCDA | 29,000 | | | | |
| Day 76 | Day 90 | CDBA | 61,000 | | | | |
| Day 90 | Day 121 | DABC | 137,500 | | | | |

The productivity for Cycle 1 was calculated as the sum of all of the oil pumped during the time the reactor was online (190,000 kg) divided by the amount of enzyme the oil was in contact with (80 kg), yielding a productivity of 2.38 kg of oil per gram of enzyme. The productivity of all of the cycles is in Table 20. It may be seen that ail of these values are substantial improvements over the prior art processes of Examples 1-3, and even over the bench scale process of the invention of Example 5

TABLE 20

| Cycle | Total Production (kg) | Total Enzyme (kg) | Productivity (kg/g) |
|---|---|---|---|
| 1 | 190,000 | 80 | 2.38 |
| 2 | 191,000 | 80 | 2.38 |
| 3 | 166,000 | 80 | 2.08 |
| 4 | 283,000 | 80 | 3.54 |

Differences in the productivity during the trial can be attributed to periods where the enzymatic interesterification system was not utilized for periods of time due to plant maintenance and plant operational shut downs. It is expected that a productivity of about 3.5 kg/g will be achieved at 100% utilization of enzyme in the industrial reactors and when pretreatment reactors of the type generally indicated as column type "3" in FIG. 5 are placed online. The examples clearly demonstrate the utility of the multiple reactor system and the unexpected advantages of a substantially moisture free silica as a pretreatment processing aid for improvement and economic commercialization for a continuous enzymatic process.

There have been disclosed herein a method and apparatus for the continuous enzymatic treatment of a lipid-containing composition, preferably with a pre-treatment system, wherein either the treatment or the pre-treatment or both occurs in a plurality of treatment modules connected in series, the modules arranged such that one of the them can be taken offline while the system is operating, thereby ensuring continuous operation. The method and apparatus significantly extend the life of the enzyme, and provide more efficient use of the entire enzyme in the treatment modules. The invention further comprises and EIE process using a pretreatment process aid of substantially moisture free silica, used either in a separate pre-treatment reactor or system, or placed above the enzyme in each reaction column.

We claim:

1. A system for continuous treatment of a lipid-containing composition, the system comprising
   a feedstock inlet,
   a product outlet,
   a plurality of continuous enzyme-containing fixed bed reactors disposed between said inlet and said outlet,
   means for pre-treating said lipid-containing composition with a process aid before the composition contacts an enzyme in at least one of said plurality of fixed bed reactors, wherein the process aid comprises a silica having an average pore size of greater than 150 Angstroms and less than 10% volatiles by weight, wherein the ratio of silica to enzyme is not greater than 50% by weight, and
   an adjustable fluid communication means for connecting said fixed bed reactors to one another in series, such that feed stock flows into said system through said inlet, then through the means for pre-treating said lipid-containing composition, then through said serially connected fixed bed reactors, and finally out of said system as a treated product through said outlet, said fluid communication means being adjustable so as to allow one of said fixed bed reactors to be taken off line while the other fixed bed reactor or reactors in said series remains in fluid communication with said system, while the flow of the lipid-containing composition through said system remains substantially constant and wherein the rate of reaction of enzyme and the lipid-containing composition does not decrease substantially as the lipid-containing composition proceeds through the reactors.

2. The system of claim 1, wherein said silica is selected from one or more of the group consisting of chromatographic silica, fused silica, precipitated silica, fumed silica, colloidal silica, amorphous silica, and silica hydrogel.

3. The system of claim 1, wherein the ratio of substantially moisture-free silica to enzyme is no greater than 25%.

4. The system of claim 1, wherein said silica contains less than about 5% volatiles by weight.

5. The system of claim 1, wherein said silica when analyzed on a dry basis is at least 95% $SiO_2$.

6. The system of claim 1, wherein said silica when analyzed on a dry basis is at least 99% $SiO_2$.

7. The system of claim 1, wherein said silica product has an average pore size of greater than 160 Angstroms.

8. The system of claim 1, wherein said silica has a pH of lower than about 7.0.

9. The system of claim 1, wherein said means for pre-treating said lipid-containing composition comprises a quantity of said process aid disposed in at least one of said plurality of fixed bed reactors such that lipid-containing composition flowing into said reactor contacts said process aid before said lipid-containing composition contacts said enzyme disposed therein.

10. The system of claim 1, wherein said means for pre-treating said lipid-containing composition comprises one or more pre-treatment reactors containing a quantity of said process aid, said one or more pre-treatment reactors disposed in series with and upstream of said plurality of fixed bed reactors.

11. The system of claim 1, wherein said enzyme is selected from one or more of the group consisting of lipase; esterase; acylase; those enzymes that facilitate acidolysis reactions, transesterification reactions, ester synthesis, or ester interchange reactions; and enzymes having phospholipase or protease activity, including thermostable and thermotolerant hydrolase activity.

12. The system of claim 1, wherein said lipid containing composition contains one or more oils or fats selected from the group consisting of canola oil, castor oil, coconut oil, coriander oil, corn oil, cottonseed oil, hazelnut oil, hempseed oil, linseed oil, meadowfoam oil, olive oil, palm oil, palm kernel oil, peanut oil, rapeseed oil, rice bran oil, safflower oil, sasanqua oil, soybean oil, sunflower seed oil, tall oil, tsubaki oil, high oleic oil, low linolenic oil, low saturated oil vegetable oil, menhaden, candlefish oil, cod-liver oil, orange roughy oil, sardine oil, herring oils, lard, tallow, and blends of any of the foregoing.

13. The method of claim 1 wherein said feedstock comprises lipid materials that have been 1) refined and bleached; 2) refined, bleached, and partially hydrogenated; 3) refined, bleached, and fully hydrogenated; or 4) refined, bleached, and fractionated.

14. The system of claim 1, wherein said lipid containing composition contains one or more oils or fats selected from the group consisting of high oleic canola oil, low linolenic soybean oil or high stearic sunflower oil.

* * * * *